United States Patent
Jackson et al.

(10) Patent No.: US 10,288,627 B2
(45) Date of Patent: May 14, 2019

(54) ASSAY FOR PRIONS

(75) Inventors: Graham Stuart Jackson, London (GB); John Collinge, London (GB); Julie Ann Edgeworth, London (GB)

(73) Assignee: D-Gen Limited, London (GB)

( * ) Notice: Subject to any disclaimer, the term of this patent is extended or adjusted under 35 U.S.C. 154(b) by 333 days.

(21) Appl. No.: 13/824,307

(22) PCT Filed: Sep. 13, 2011

(86) PCT No.: PCT/GB2011/001341
§ 371 (c)(1),
(2), (4) Date: Mar. 15, 2013

(87) PCT Pub. No.: WO2012/035296
PCT Pub. Date: Mar. 22, 2012

(65) Prior Publication Data
US 2013/0196356 A1    Aug. 1, 2013

(30) Foreign Application Priority Data
Sep. 16, 2010 (GB) .................................. 1015569.5

(51) Int. Cl.
G01N 33/68 (2006.01)

(52) U.S. Cl.
CPC ..... G01N 33/6896 (2013.01); G01N 33/6893 (2013.01); G01N 2333/70596 (2013.01); G01N 2800/2828 (2013.01)

(58) Field of Classification Search
None
See application file for complete search history.

(56) References Cited

U.S. PATENT DOCUMENTS

| | | | |
|---|---|---|---|
| 7,344,842 B1 * | 3/2008 | Garssen et al. | 435/7.1 |
| 7,582,465 B2 * | 9/2009 | Citron et al. | 435/252.3 |
| 2003/0044868 A1 * | 3/2003 | Aslamkhan et al. | 435/7.92 |
| 2004/0018554 A1 * | 1/2004 | Green | 435/7.1 |
| 2004/0115730 A1 * | 6/2004 | O'Connor | 435/7.1 |
| 2005/0158807 A1 * | 7/2005 | Chiocchia et al. | 435/7.23 |
| 2005/0202400 A1 * | 9/2005 | Tsuji | G01N 33/52 435/4 |
| 2005/0221320 A1 * | 10/2005 | Enari et al. | 435/6 |
| 2006/0030535 A1 * | 2/2006 | Healy et al. | 514/44 |
| 2008/0108085 A1 * | 5/2008 | Enari et al. | 435/7.1 |
| 2008/0254486 A1 * | 10/2008 | Hayward et al. | 435/7.8 |
| 2009/0048162 A1 * | 2/2009 | Ko et al. | 514/12 |
| 2009/0130774 A1 * | 5/2009 | Peretz et al. | 436/501 |

FOREIGN PATENT DOCUMENTS

| | | |
|---|---|---|
| WO | WO 9015666 A1 * | 12/1990 |
| WO | 01/71361 A2 | 9/2001 |
| WO | 02/059615 A2 | 8/2002 |
| WO | 2008/013885 A2 | 1/2008 |
| WO | 2009/040508 A2 | 4/2009 |

OTHER PUBLICATIONS

Luhr et al. Prion adsorption to stainless steel is promoted by nickel and molybdenum, Journal of General Virology, 90, (2009), p. 2821-2828.*
Goodfellow Catalogue (Web. http://www.furuchi.co.jp/material/img/goodfellow_catalog.pdf. Published Feb. 2009. Accessed May 1, 2014. pp. 80-83).*
Sigma (Web: http/www.sigmaaldrich.com/catalog/product/sigma/19899?lang-en®ion=US. Accessed May 5, 2014).*
Harlow & Lane (Harlow, E. and Lane, D., Antibodies: A Laboratory Manual (1988) Cold Spring Harbor Laboratory Press, Cold Spring Harbor, NY, p. 447, 460, 680.).*
Edgeworth, J. A. et al., "Detection of prion infection in variant Creutzfeldt-Jakob disease: a blood-based assay," Lancet, Lancet Limited. London, GB, vol. 377, No. 9764, Feb. 5, 2011, pp. 487-493, XP009156074.
Edgeworth, J.A. et al., "Highly sensitive, quantitative cell-based assay for prions adsorbed to solid surfaces," National Academy of Sciences. Proceedings, National Academy of Sciences, U.S., vol. 106, No. 9, Mar. 3, 2009, pp. 3479-3483, XP009156111.
Pal, S. et al, "A novel Method for Immunodiagnosis of Variant Creutzfeldt-Jakob Disease," Journal of Neurology Neursurgery & Psychiatry, BMJ Publishing Group, GB, vol. 78, No. 2, Jan. 1, 2007, p. 207, XP009111972.
The International Search Report, dated Mar. 2, 2012, in related International patent application No. PCT/GB2011/001341, filed Sep. 13, 2011.
Search Report, dated Feb. 24, 2011, in related GB application No. GB1015569.5, filed Sep. 16, 2010.

* cited by examiner

*Primary Examiner* — Ram R Shukla
*Assistant Examiner* — Ellen J Marcsisin
(74) *Attorney, Agent, or Firm* — Wiley Rein LLP

(57) ABSTRACT

The invention relates to a method for detection of abnormal PrP in a sample of blood or urine, said method comprising: (a) diluting the sample with buffer to comprise final concentrations of (i) 10 mM to 500 mM buffer agent; (ii) 1% to 10% w/v bovine serum albumin; and (iii) 1% to 8% w/v CHAPS; (b) adding steel particles and incubating to allow PrP binding; (c) washing the steel particles to remove diluted sample; and (d) detecting abnormal PrP captured on the steel particles using antibody capable of binding said abnormal PrP. The invention also provides compositions and kits.

10 Claims, 11 Drawing Sheets

Specification includes a Sequence Listing.

FIG. 4

ICSM33 VH sequence
MEWIWVFLFLLSVIEGVHSQVQLQQSGPELVKPGASVKISCKASGY
AFSNSWMNWVKQRPGKGLEWIGRIYLGDGDTNYNGKFKGKATLTA
DKSSNTAYMQLSSLTSEDSAVYFCARAPLRYPYFDYWGQGTTLTVSS
A

```
MEWIWVFLFLLSVIEGVHSQVQLQQSGPELVKPGASVKIS                40
+----+----+----+----+----+----+----+----+
         <leader>

CKASGYAFSNSWMNWVKQRPGKGLEWIGRIYLGDGDTNYN                80
+----+----+----+----+----+----+----+----+
        <CDR1>              <CDR2>

GKFKGKATLTADKSSNTAYMQLSSLTSEDSAVYFCARAPL               120
+----+----+----+----+----+----+----+----+
<CDR2>

RYPYFDYWGQGTTLTVSSA                                    139
+----+----+----+----+
<CDR3>
```

ICSM33 VK sequence
MVSTAQFLGLLLLCFQGTRCDIQMTQTTSSLSASLGDRVTISCRASQ
DISNYLNWYQQKPDGTVKLLISYTSRLHSGVPSRFSGSGSGTDYFLTIS
NLEQEDIATYFCQQGNTLPPTFGGGTKLEIKRADAAPTVS

```
MVSTAQFLGLLLLCFQGTRCDIQMTQTTSSLSASLGDRVT                40
+----+----+----+----+----+----+----+----+
         <leader>

ISCRASQDISNYLNWYQQKPDGTVKLLISYTSRLHSGVPS                80
+----+----+----+----+----+----+----+----+
       <CDR1>                <CDR2>

RFSGSGSGTDYFLTISNLEQEDIATYFCQQGNTLPPTFGG               120
+----+----+----+----+----+----+----+----+
                           <CDR3>

GTKLEIKRADAAPTVS                                       136
+----+----+----+
     <constant>
```

FIG. 5
ICSM35VH sequence

```
ATGGAATGGACCTGGGTCATTCTCTTCCTCCTGTCAGTAACTGAAGGTGTCCACTCCCAG
                                                              60
         Leader sequence
M  E  W  T  W  V  I  L  F  L  L  S  V  T  E  G  V  H  S  Q GTTCAGCTGCAGCAGTCTGGACCTGAGCTGGTGAAGCCTGGGGCCTCAGTGAAGATTTCC
                                                              120
V  Q  L  Q  Q  S  G  P  E  L  V  K  P  G  A  S  V  K  I  S TGCAAGGCTTCTGGCTACACATTCAGTAACTCCTGGATGAACTGGGTGAAGCAGAGGCCT
                                                              180
                                    CDR1
C  K  A  S  G  Y  T  F  S  N  S  W  M  N  W  V  K  Q  R  P GGAAAGGTCTTGAGTGGATTGGACGGATTTATCCTGAATATGGACATGCTGACTACAAT
                                                              240
                          CDR2
G  K  G  L  E  W  I  G  R  I  Y  P  E  Y  G  H  A  D  Y  N GGGAAGTTCAAGGCAAGGCCACACTGACTGCTGACAGATCCTCCAGCACAGCCTACATG
                                                              300
       CDR3
G  K  F  K  G  K  A  T  L  T  A  D  R  S  S  S  T  A  Y  M CACCTCAGCAGCCTGACGTCTGAGGACTCTGCGGTCTACTTCTGTGCACGAGCCCCACTA
                                                              360
                                                     CDR3
H  L  S  S  L  T  S  E  D  S  A  V  Y  F  C  A  R  A  P  L CGGTACCCCTACTTTGACTACTGGGGCCAAGGCACCACTCTCACAGTCTCCTCA
                                                              414
           CDR3
R  Y  P  Y  F  D  Y  W  G  Q  G  T  T  L  T  V  S  S
```

ATGGAATGGACCTGGGTCATTCTCTTCCTCCTGTCAGTAACTGAAGGTGT
CCACTCCCAGGTTCAGCTGCAGCAGTCTGGACCTGAGCTGGTGAAGCCTG
GGGCCTCAGTGAAGATTTCCTGCAAGGCTTCTGGCTACACATTCAGTAAC
TCCTGGATGAACTGGGTGAAGCAGAGGCCTGGGAAAGGTCTTGAGTGGAT
TGGACGGATTTATCCTGAATATGGACATGCTGACTACAATGGGAAGTTCG
AAGGCAAGGCCACACTGACTGCTGACAGATCCTCCAGCACAGCCTACATG
CACCTCAGCAGCCTGACGTCTGAGGACTCTGCGGTCTACTTCTGTGCACG
AGCCCCACTACGGTACCCCTACTTTGACTACTGGGGCCAAGGCACCACTC
TCACAGTCTCCTCA

FIG. 6

ICSM35VK sequence

```
ATGGTGTCCACAGCTCAGTTCCTTGGTCTCCTGTTGCTCTGTTTTCAAGGTACCAGATGT
++++++++++++++++++++++++++++++++++++++++++++++++++++++++++++  60
                          leader
 M  V  S  T  A  Q  F  L  G  L  L  L  L  C  F  Q  G  T  R  C GATATCCAGATGACaCAGAcTTCATCCTCCCTGTCTGCCTCTCTGGGAGACAGAGTCTCC
++++++++++++++++++++++++++++++++++++++++++++++++++++++++++++  120
 D  I  Q  M  T  Q  S  S  L  S  A  S  L  G  D  R  V  S ATCAGTTGCAGGGCAAGTCAGGACATTTCCAATTATTTAAACTGGTATCAGCAGAaACCA
++++++++++++++++++++++++++++++++++++++++++++++++++++++++++++  180
                       CDR1
 I  S  C  R  A  S  Q  D  I  S  N  Y  L  N  W  Y  Q  Q  K  P GATGGAACTGTTAAACTCCTGATCCACTACACATCAAGATTACACTCAGGAGTCCCATCA
++++++++++++++++++++++++++++++++++++++++++++++++++++++++++++  240
                         CDR2
 D  G  T  V  K  L  L  I  H  Y  T  S  R  L  H  S  G  V  P  S AGGTtCAGTGGCAGTGGGTCTGGAACAGATTATTCTCTCACCATTAGCCACCTGGAGGAA
++++++++++++++++++++++++++++++++++++++++++++++++++++++++++++  300
 R  F  S  G  S  G  S  G  T  D  Y  S  L  T  I  S  H  L  E  E GAAGATATTGCCACTTACTTTTGCCAACAGGGTAATGCGcTTCCTCCGACGTTCGGTGGC
++++++++++++++++++++++++++++++++++++++++++++++++++++++++++++  360
                              CDR3
 E  D  I  A  T  Y  F  C  Q  Q  G  N  A  L  P  P  T  F  G  G

GGCACCAAGCTGGAAATCAAA
+++++++++++++++++++++  381
 G  T  K  L  E  I  K
```

ATGGTGTCCACAGCTCAGTTCCTTGGTCTCCTGTTGCTCTGTTTTCAAGG
TACCAGATGTGATATCCAGATGACaCAGAcTTCATCCTCCCTGTCTGCCT
CTCTGGGAGACAGAGTCTCCATCAGTTGC AGGGCAAGTCAGGACATTTCC
AATTATTTAAAC TGGTATCAGCAGAaACCAGATGGAACTGTTAAACTCCT
GATCCAC TACACATCAAGATTACACTCA GGAGTCCCATCAAGGTtCAGTG
GCAGTGGGTCTGGAACAGATTATTCTCTCACCATTAGCCACCTGGAGGAA
GAAGATATTGCCACTTACTTTTGC CAACAGGGTAATGCGcTTCCTCCGAC
G TTCGGTGGCGGCACCAAGCTGGAAATCAAA

Fig. 7
ICSM18VH sequence

```
ATGGAATGGAGCTGGGTTTTCCTCTTCCTCCTGTCAGGAACTGCAGGTGTCCTCTCTGAG
++++|++++|++++|++++|++++|++++|++++|++++|++++|++++|++++|++++|  60
                            leader
  M  E  W  S  W  V  F  L  F  L  L  S  G  T  A  G  V  L  S  E GTCCAGCTACAACAGTCTGGACCTGAGCTGGTGAAGCCTGGGTCTTCAGTGAAgATATCC
++++|++++|++++|++++|++++|++++|++++|++++|++++|++++|++++|++++| 120
  V  Q  L  Q  Q  S  G  P  E  L  V  K  P  G  S  S  V  K  I  S TGCAAGGCATCTAGAAACACATTCACTGACTATAACTTGGACTGGGTGAAGCAGAGCCAT
++++|++++|++++|++++|++++|++++|++++|++++|++++|++++|++++|++++| 180
                            CDR1
  C  K  A  S  R  N  T  F  T  D  Y  N  L  D  W  V  K  Q  S  H GGAAAGACACTTGAGTGGATTGGAAATGTTTATCCTAACAATGGTGTTACTGGCTACAAC
++++|++++|++++|++++|++++|++++|++++|++++|++++|++++|++++|++++| 240
                         CDR2
  G  K  T  L  E  W  I  G  N  V  Y  P  N  N  G  V  T  G  Y  N CAgAAgTTCAGGGGTAAGGCCACACTGACTGTAgACAAGTCCTCCAGCACAGCCTACATG
++++|++++|++++|++++|++++|++++|++++|++++|++++|++++|++++|++++| 300
       CDR2
  Q  K  F  R  G  K  A  T  L  T  V  D  K  S  S  S  T  A  Y  M GAGCTCCACAGCCTGACATCTGAGGACTCTGCAGTCTATTACTGTGCCCTTTATTACTAC
++++|++++|++++|++++|++++|++++|++++|++++|++++|++++|++++|++++| 360
                                                  CDR3
  E  L  H  S  L  T  S  E  D  S  A  V  Y  Y  C  A  L  Y  Y  Y gATgTCTCTTACTGGGGCCAAGGGACTCTGGTCACTGTCTCTGCA
++++|++++|++++|++++|++++|++++|++++|++++|++++| 405
    CDR3
  D  V  S  Y  W  G  Q  G  T  L  V  T  V  S  A
```

ATGGAATGGAGCTGGGTTTTCCTCTTCCTCCTGTCAGGAACTGCAGGTGT
CCTCTCTGAGGTCCAGCTACAACAGTCTGGACCTGAGCTGGTGAAGCCTG
GGTCTTCAGTGAAgATATCCTGCAAGGCATCTAGAAACACATTCACT GAC
TATAACTTGGAC TGGGTGAAGCAGAGCCATGGAAAGACACTTGAGTGGAT
TGGA AATGTTTATCCTAACAATGGTGTTACTGGCTACAACCAgAAgTTCA
GGGGT AAGGCCACACTGACTGTAgACAAGTCCTCCAGCACAGCCTACATG
GAGCTCCACAGCCTGACATCTGAGGACTCTGCAGTCTATTACTGTGCCCT
T TATTACTACgATgTCTCTTAC TGGGGCCAAGGGACTCTGGTCACTGTCT
CTGCA

FIG. 8A
ICSM181c sequence

```
ATGGATTTACAGGTGCAGATTATCAGCTTCCTGCTAATCAGTGCCTCAGTCATAATATCC   60
                          leader
 M  D  L  Q  V  Q  I  S  F  L  L  I  S  A  S  V  I  S AGAGGACAAATTGTTCTCACCCAGTCTCCAGCAATCATGTCTGCATCTCCAGGGGAGAAg  120
     leader
 R  G  Q  I  V  L  T  Q  S  P  A  I  M  S  A  S  P  G  E  K GTCACCATGACCTGCAGTGCCAGCTCAAGTGTAAGTTACATGCACTGGTACCAGCAGAAG  180
                            CDR1
 V  T  M  T  C  S  A  S  S  S  V  S  Y  M  H  W  Y  Q  Q  K TCAGGCACCTCCCCCAAAAGATGGATTTATGACACATCCAAACTGGCTTCTGGAGTCCCT  240
                                  CDR2
 S  G  T  S  P  K  R  W  I  Y  D  T  S  K  L  A  S  G  V  P GCTCGCTTCAGTGGCAGTGGGTCTGGGACCTCTTACTCTCTCACAATCAGCAGTATGGAG  300
 A  R  F  S  G  S  G  S  G  T  S  Y  S  L  T  I  S  S  M  E GCTGAAGATGCTGCCACTTATTTCTGCCACCAGTGGAGAAgTAACCCATACACGTTCGGA  360
                                CDR3
 A  E  D  A  A  T  Y  F  C  H  Q  W  R  S  N  P  Y  T  F  G GGGGGGACCAAGCTGGAAATAAAACGGGCTGATGCTGCACCAACTGTATCCATCTTCCCA  420
                                          Constant Region
 G  G  T  K  L  E  I  K  R  A  D  A  A  P  T  V  S  I  F  P CCATCCAGTGAGCAGTTAACATCTGGAGGTGCCTCAGTCGTGTGCTTCTTGAACAACTTC  480
                          Constant Region
 P  S  S  E  Q  L  T  S  G  G  A  S  V  V  C  F  L  N  N  F TACCCCAAAGACATCAATGTCAAGTGGAAGATTGATGGCAGTGAACGACAAAATGGCGTC  540
                          Constant Region
 Y  P  K  D  I  N  V  K  W  K  I  D  G  S  E  R  Q  N  G  V CTGAACAGTTGGACTGATCAGGACAGCAAAGACAGCACCTACAGCATGAGCAGCACCCTC  600
                          Constant Region
 L  N  S  W  T  D  Q  D  S  K  D  S  T  Y  S  M  S  S  T  L ACGTTGACCAAGGACGAGTATGAACGACATAACAGCTATACCTGTGAGGCCACTCACAAG  660
                          Constant Region
 T  L  T  K  D  E  Y  E  R  H  N  S  Y  T  C  E  A  T  H  K ACATCAACTTCACCCATTGTCAAGAGCTTCAACAGGGGAGAGTGTTAGTGA          711
                          Constant Region
 T  S  T  S  P  I  V  K  S  F  N  R  G  E  C  .  .
```

FIG. 8B
ATGGATTTACAGGTGCAGATTATCAGCTTCCTGCTAATCAGTGCCTCAGT
CATAATATCCAGAGGACAAATTGTTCTCACCCAGTCTCCAGCAATCATGT
CTGCATCTCCAGGGGAGAAgGTCACCATGACCTGCAGTGCCAGCTCAAGT
GTAAGTTACATGCACTGGTACCAGCAGAAGTCAGGCACCTCCCCCAAAAG
ATGGATTTATGACACATCCAAACTGGCTTCTGGAGTCCCTGCTCGCTTCA
GTGGCAGTGGGTCTGGGACCTCTTACTCTCTCACAATCAGCAGTATGGAG
GCTGAAGATGCTGCCACTTATTTCTGCCACCAGTGGAGAAgTAACCCATA
CACGTTCGGAGGGGGGACCAAGCTGGAAATAAAACGGGCTGATGCTGCAC
CAACTGTATCCATCTTCCCACCATCCAGTGAGCAGTTAACATCTGGAGGT
GCCTCAGTCGTGTGCTTCTTGAACAACTTCTACCCCAAAGACATCAATGT
CAAGTGGAAGATTGATGGCAGTGAACGACAAAATGGCGTCCTGAACAGTT
GGACTGATCAGGACAGCAAAGACAGCACCTACAGCATGAGCAGCACCCTC
ACGTTGACCAAGGACGAGTATGAACGACATAACAGCTATACCTGTGAGGC
CACTCACAAGACATCAACTTCACCCATTGTCAAGAGCTTCAACAGGGGAG
AGTGTTAGTGA

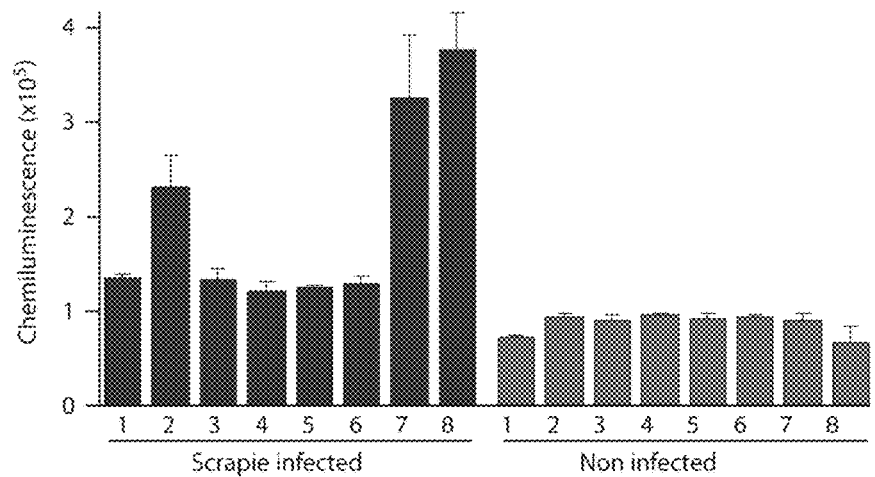

FIG. 9

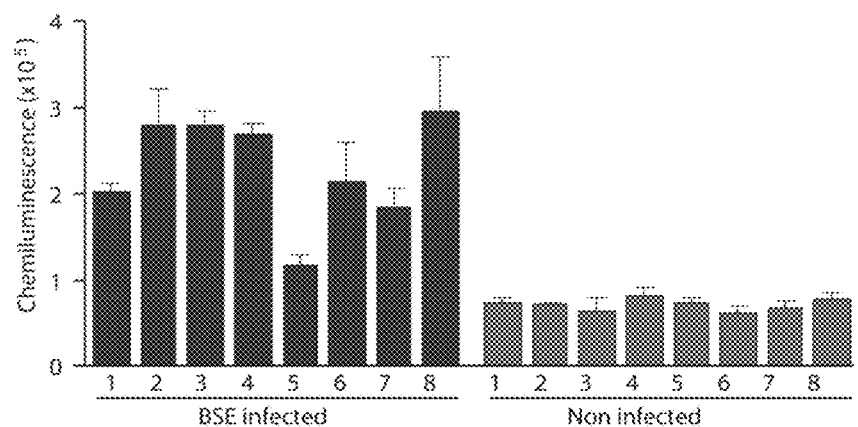

FIG. 10

MANLGCWMLVLFVATWSDLGLCKKRPKPGGWNTGGSRYPGQGSPGGNRYPP
QGGGWGQPHGGGWGQPHGGGWGQPHGGGWGQPHGGGWGQGGGTHSQWNKP
SKPKTNMKHMAGAAAAGAVVGGLGGYMLGSAMSRPIIHFGSDYEDRYYREN
MHRYPNQVYYRPMDEYSNQNNFVHDCVNITIKQHTVTTTTKGENFTETDVK
MMERVVEQMCITQYERESQAYYQRGSSMVLFSSPPVILLISFLIFLIVG

SEQUENCE LISTING

<160> NUMBER OF SEQ ID NOS: 11

<210> SEQ ID NO 1
<211> LENGTH: 414
<212> TYPE: DNA
<213> ORGANISM: Artificial Sequence
<220> FEATURE:
<223> OTHER INFORMATION: ICSM35VH

<400> SEQUENCE: 1

```
atggaatgga cctgggtcat tctcttcctc ctgtcagtaa ctgaaggtgt ccactcccag      60
gttcagctgc agcagtctgg acctgagctg gtgaagcctg gggcctcagt gaagatttcc     120
tgcaaggctt ctggctacac attcagtaac tcctggatga actgggtgaa gcagaggcct     180
gggaaaggtc ttgagtggat tggacggatt tatcctgaat atggacatgc tgactacaat     240
gggaagttcg aaggcaaggc cacactgact gctgacagat cctccagcac agcctacatg     300
cacctcagca gcctgacgtc tgaggactct gcggtctact tctgtgcacg agccccacta     360
cggtacccct actttgacta ctggggccaa ggcaccactc tcacagtctc ctca           414
```

<210> SEQ ID NO 2
<211> LENGTH: 381
<212> TYPE: DNA
<213> ORGANISM: Artificial Sequence
<220> FEATURE:
<223> OTHER INFORMATION: ICSM35VK

<400> SEQUENCE: 2

```
atggtgtcca cagctcagtt ccttggtctc ctgttgctct gttttcaagg taccagatgt      60
```

```
gatatccaga tgacacagac ttcatcctcc ctgtctgcct ctctgggaga cagagtctcc    120
atcagttgca gggcaagtca ggacatttcc aattatttaa actggtatca gcagaaacca    180
gatggaactg ttaaactcct gatccactac acatcaagat tacactcagg agtcccatca    240
aggttcagtg gcagtgggtc tggaacagat tattctctca ccattagcca cctggaggaa    300
gaagatattg ccacttactt tgccaacagg gtaatgcgc ttcctccgac gttcggtggc     360
ggcaccaagc tggaaatcaa a                                              381

<210> SEQ ID NO 3
<211> LENGTH: 405
<212> TYPE: DNA
<213> ORGANISM: Artificial Sequence
<220> FEATURE:
<223> OTHER INFORMATION: ICSM18VH

<400> SEQUENCE: 3
atggaatgga gctgggtttt cctcttcctc ctgtcaggaa ctgcaggtgt cctctctgag     60
gtccagctac aacagtctgg acctgagctg gtgaagcctg ggtcttcagt gaagatatcc    120
tgcaaggcat ctagaaacac attcactgac tataacttgg actgggtgaa gcagagccat    180
ggaaagacac ttgagtggat tggaaatgtt tatcctaaca atggtgttac tggctacaac    240
cagaagttca gggtaaggc cacactgact gtagacaagt cctccagcac agcctacatg     300
gagctccaca gcctgacatc tgaggactct gcagtctatt actgtgccct ttattactac    360
gatgtctctt actggggcca aggaactctg gtcactgtct ctgca                    405

<210> SEQ ID NO 4
<211> LENGTH: 711
<212> TYPE: DNA
<213> ORGANISM: Artificial Sequence
<220> FEATURE:
<223> OTHER INFORMATION: ICSM18lc

<400> SEQUENCE: 4
atggatttac aggtgcagat tatcagcttc ctgctaatca gtgcctcagt cataatatcc     60
agaggacaaa ttgttctcac ccagtctcca gcaatcatgt ctgcatctcc aggggagaag    120
gtcaccatga cctgcagtgc cagctcaagt gtaagttaca tgcactggta ccagcagaag    180
tcaggcacct cccccaaaag atggatttat gacacatcca aactggcttc tggagtccct    240
gctcgcttca gtggcagtgg gtctgggacc tcttactctc tcacaatcag cagtatggag    300
gctgaagatg ctgccactta tttctgccac cagtggagaa gtaacccata cacgttcgga    360
ggggggacca gctggaaat aaaacgggct gatgctgcac caactgtatc catcttccca    420
ccatccagtg agcagttaac atctggaggt gcctcagtcg tgtgcttctt gaacaacttc    480
taccccaaag acatcaatgt caagtggaag attgatggca gtgaacgaca aaatggcgtc    540
ctgaacagtt ggactgatca ggacagcaaa gacagcacct acagcatgag cagcaccctc    600
acgttgacca aggacgagta tgaacgacat aacagctata cctgtgaggc cactcacaag    660
acatcaactt cacccattgt caagagcttc aacaggggag agtgttagtg a             711

<210> SEQ ID NO 5
<211> LENGTH: 139
<212> TYPE: PRT
<213> ORGANISM: Artificial Sequence
<220> FEATURE:
<223> OTHER INFORMATION: ICSM33 VH

<400> SEQUENCE: 5
```

```
Met Glu Trp Thr Trp Val Phe Leu Phe Leu Leu Ser Val Thr Glu Gly
1               5                   10                  15

Val His Ser Gln Val Gln Leu Gln Gln Ser Gly Pro Glu Leu Val Lys
            20                  25                  30

Pro Gly Ala Ser Val Lys Ile Ser Cys Lys Ala Ser Gly Tyr Ala Phe
        35                  40                  45

Ser Asn Ser Trp Met Asn Trp Val Lys Gln Arg Pro Gly Lys Gly Leu
    50                  55                  60

Glu Trp Ile Gly Arg Ile Tyr Leu Gly Asp Gly Asp Thr Asn Tyr Asn
65                  70                  75                  80

Gly Lys Phe Lys Gly Lys Ala Thr Leu Thr Ala Asp Lys Ser Ser Asn
                85                  90                  95

Thr Ala Tyr Met Gln Leu Ser Ser Leu Thr Ser Glu Asp Ser Ala Val
            100                 105                 110

Tyr Phe Cys Ala Arg Ala Pro Leu Arg Tyr Pro Tyr Phe Asp Tyr Trp
        115                 120                 125

Gly Gln Gly Thr Thr Leu Thr Val Ser Ser Ala
        130                 135
```

<210> SEQ ID NO 6
<211> LENGTH: 136
<212> TYPE: PRT
<213> ORGANISM: Artificial Sequence
<220> FEATURE:
<223> OTHER INFORMATION: ICSM33 VK

<400> SEQUENCE: 6

```
Met Val Ser Thr Ala Gln Phe Leu Gly Leu Leu Leu Cys Phe Gln
1               5                   10                  15

Gly Thr Arg Cys Asp Ile Gln Met Thr Gln Thr Thr Ser Ser Leu Ser
            20                  25                  30

Ala Ser Leu Gly Asp Arg Val Thr Ile Ser Cys Arg Ala Ser Gln Asp
        35                  40                  45

Ile Ser Asn Tyr Leu Asn Trp Tyr Gln Gln Lys Pro Asp Gly Thr Val
    50                  55                  60

Lys Leu Leu Ile Ser Tyr Thr Ser Arg Leu His Ser Gly Val Pro Ser
65                  70                  75                  80

Arg Phe Ser Gly Ser Gly Ser Gly Thr Asp Tyr Phe Leu Thr Ile Ser
                85                  90                  95

Asn Leu Glu Gln Glu Asp Ile Ala Thr Tyr Phe Cys Gln Gln Gly Asn
            100                 105                 110

Thr Leu Pro Pro Thr Phe Gly Gly Gly Thr Lys Leu Glu Ile Lys Arg
        115                 120                 125

Ala Asp Ala Ala Pro Thr Val Ser
        130                 135
```

<210> SEQ ID NO 7
<211> LENGTH: 253
<212> TYPE: PRT
<213> ORGANISM: Homo sapiens

<400> SEQUENCE: 7

```
Met Ala Asn Leu Gly Cys Trp Met Leu Val Leu Phe Val Ala Thr Trp
1               5                   10                  15

Ser Asp Leu Gly Leu Cys Lys Lys Arg Pro Lys Pro Gly Gly Trp Asn
            20                  25                  30
```

Thr Gly Gly Ser Arg Tyr Pro Gly Gln Gly Ser Pro Gly Asn Arg
            35                  40                  45

Tyr Pro Pro Gln Gly Gly Gly Trp Gly Gln Pro His Gly Gly Gly
 50                  55                  60

Trp Gly Gln Pro His Gly Gly Gly Trp Gly Gln Pro His Gly Gly
 65                  70                  75                  80

Trp Gly Gln Pro His Gly Gly Gly Trp Gly Gln Gly Gly Gly Thr His
                    85                  90                  95

Ser Gln Trp Asn Lys Pro Ser Lys Pro Lys Thr Asn Met Lys His Met
                100                 105                 110

Ala Gly Ala Ala Ala Ala Gly Ala Val Val Gly Gly Leu Gly Gly Tyr
            115                 120                 125

Met Leu Gly Ser Ala Met Ser Arg Pro Ile Ile His Phe Gly Ser Asp
    130                 135                 140

Tyr Glu Asp Arg Tyr Tyr Arg Glu Asn Met His Arg Tyr Pro Asn Gln
145                 150                 155                 160

Val Tyr Tyr Arg Pro Met Asp Glu Tyr Ser Asn Gln Asn Asn Phe Val
                165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Val Lys Met Met Glu Arg
    195                 200                 205

Val Val Glu Gln Met Cys Ile Thr Gln Tyr Glu Arg Glu Ser Gln Ala
210                 215                 220

Tyr Tyr Gln Arg Gly Ser Ser Met Val Leu Phe Ser Ser Pro Pro Val
225                 230                 235                 240

Ile Leu Leu Ile Ser Phe Leu Ile Phe Leu Ile Val Gly
                245                 250

<210> SEQ ID NO 8
<211> LENGTH: 118
<212> TYPE: PRT
<213> ORGANISM: artificial sequence
<220> FEATURE:
<223> OTHER INFORMATION: ICSM35 VH

<400> SEQUENCE: 8

Met Glu Trp Thr Trp Val Ile Leu Phe Leu Leu Ser Val Thr Glu Gly
 1               5                   10                  15

Val His Ser Gln Val Gln Leu Gln Gln Ser Gly Pro Glu Leu Val Lys
            20                  25                  30

Pro Gly Ala Ser Val Lys Ile Ser Cys Lys Ala Ser Gly Tyr Thr Phe
        35                  40                  45

Ser Asn Ser Trp Met Asn Trp Val Lys Gln Arg Pro Gly Lys Gly Leu
    50                  55                  60

Glu Trp Ile Gly Arg Ile Tyr Pro Glu Tyr Gly His Ala Asp Tyr Asn
65                  70                  75                  80

His Leu Ser Ser Leu Thr Ser Glu Asp Ser Ala Val Tyr Phe Cys Ala
                85                  90                  95

Arg Ala Pro Leu Arg Tyr Pro Tyr Phe Asp Tyr Trp Gly Gln Gly Thr
            100                 105                 110

Thr Leu Thr Val Ser Ser
        115

<210> SEQ ID NO 9
<211> LENGTH: 127

<212> TYPE: PRT
<213> ORGANISM: Artificial Sequence
<220> FEATURE:
<223> OTHER INFORMATION: ICSM35VK

<400> SEQUENCE: 9

Met Val Ser Thr Ala Gln Phe Leu Gly Leu Leu Leu Cys Phe Gln
1               5                   10                  15

Gly Thr Arg Cys Asp Ile Gln Met Thr Gln Thr Ser Ser Leu Ser
            20                  25                  30

Ala Ser Leu Gly Asp Arg Val Ser Ile Ser Cys Arg Ala Ser Gln Asp
        35                  40                  45

Ile Ser Asn Tyr Leu Asn Trp Tyr Gln Gln Lys Pro Asp Gly Thr Val
    50                  55                  60

Lys Leu Leu Ile His Tyr Thr Ser Arg Leu His Ser Gly Val Pro Ser
65                  70                  75                  80

Arg Phe Ser Gly Ser Gly Ser Gly Thr Asp Tyr Ser Leu Thr Ile Ser
                85                  90                  95

His Leu Glu Glu Glu Asp Ile Ala Thr Tyr Phe Cys Gln Gln Gly Asn
            100                 105                 110

Ala Leu Pro Pro Thr Phe Gly Gly Gly Thr Lys Leu Glu Ile Lys
        115                 120                 125

<210> SEQ ID NO 10
<211> LENGTH: 135
<212> TYPE: PRT
<213> ORGANISM: Artificial Sequence
<220> FEATURE:
<223> OTHER INFORMATION: ICSM18VH

<400> SEQUENCE: 10

Met Glu Trp Ser Trp Val Phe Leu Phe Leu Leu Ser Gly Thr Ala Gly
1               5                   10                  15

Val Leu Ser Glu Val Gln Leu Gln Gln Ser Gly Pro Glu Leu Val Lys
            20                  25                  30

Pro Gly Ser Ser Val Lys Ile Ser Cys Lys Ala Ser Arg Asn Thr Phe
        35                  40                  45

Thr Asp Tyr Asn Leu Asp Trp Val Lys Gln Ser His Gly Lys Thr Leu
    50                  55                  60

Glu Trp Ile Gly Asn Val Tyr Pro Asn Asn Gly Val Thr Gly Tyr Asn
65                  70                  75                  80

Gln Lys Phe Arg Gly Lys Ala Thr Leu Thr Val Asp Lys Ser Ser Ser
                85                  90                  95

Thr Ala Tyr Met Glu Leu His Ser Leu Thr Ser Glu Asp Ser Ala Val
            100                 105                 110

Tyr Tyr Cys Ala Leu Tyr Tyr Tyr Asp Val Ser Tyr Trp Gly Gln Gly
        115                 120                 125

Thr Leu Val Thr Val Ser Ala
    130                 135

<210> SEQ ID NO 11
<211> LENGTH: 235
<212> TYPE: PRT
<213> ORGANISM: Artificial Sequence
<220> FEATURE:
<223> OTHER INFORMATION: ICSM181c

<400> SEQUENCE: 11

Met Asp Leu Gln Val Gln Ile Ile Ser Phe Leu Leu Ile Ser Ala Ser

-continued

```
1               5                   10                  15
Val Ile Ile Ser Arg Gly Gln Ile Val Leu Thr Gln Ser Pro Ala Ile
                20                  25                  30
Met Ser Ala Ser Pro Gly Glu Lys Val Thr Met Thr Cys Ser Ala Ser
            35                  40                  45
Ser Ser Val Ser Tyr Met His Trp Tyr Gln Gln Lys Ser Gly Thr Ser
        50                  55                  60
Pro Lys Arg Trp Ile Tyr Asp Thr Ser Lys Leu Ala Ser Gly Val Pro
65                      70                  75                  80
Ala Arg Phe Ser Gly Ser Gly Ser Gly Thr Ser Tyr Ser Leu Thr Ile
                85                  90                  95
Ser Ser Met Glu Ala Glu Asp Ala Ala Thr Tyr Phe Cys His Gln Trp
            100                 105                 110
Arg Ser Asn Pro Tyr Thr Phe Gly Gly Gly Thr Lys Leu Glu Ile Lys
        115                 120                 125
Arg Ala Asp Ala Ala Pro Thr Val Ser Ile Phe Pro Pro Ser Ser Glu
    130                 135                 140
Gln Leu Thr Ser Gly Gly Ala Ser Val Val Cys Phe Leu Asn Asn Phe
145                 150                 155                 160
Tyr Pro Lys Asp Ile Asn Val Lys Trp Lys Ile Asp Gly Ser Glu Arg
                165                 170                 175
Gln Asn Gly Val Leu Asn Ser Trp Thr Asp Gln Asp Ser Lys Asp Ser
            180                 185                 190
Thr Tyr Ser Met Ser Ser Thr Leu Thr Leu Thr Lys Asp Glu Tyr Glu
        195                 200                 205
Arg His Asn Ser Tyr Thr Cys Glu Ala Thr His Lys Thr Ser Thr Ser
    210                 215                 220
Pro Ile Val Lys Ser Phe Asn Arg Gly Glu Cys
225                 230                 235
```

ASSAY FOR PRIONS

FIELD OF THE INVENTION

The invention relates to an assay for detecting prions. In particular the invention relates to an assay for detecting prion infection in blood or urine, most suitably blood.

BACKGROUND TO THE INVENTION

Prion diseases are a group of fatal neurodegenerative disorders including variant Creutzfeldt-Jakob disease (vCJD) which originates from exposure to bovine spongiform encephalopathy (BSE). Iatrogenic transmission from asymptomatic patients with vCJD prion infection via blood transfusion has had a major impact on public health policy.

Prion Disease encompasses a range of closely related and uniformly fatal neurodegenerative disorders affecting the central nervous system of humans and animals. They include Creutzfeldt-Jakob disease (CJD), Gerstmann-Sträussler-Scheinker disease (GSS), fatal familial insomnia (FFI) and kuru in humans, bovine spongiform encephalopathy (BSE) in cattle, chronic wasting disease (CWD) of deer and Elk and scrapie in sheep (1;2). The emergence of variant CJD (vCJD), and the confirmation that it originates from exposure to bovine spongiform encephalopathy (BSE) (3;4) has raised a plethora of public health concerns adversely affecting surgery, dentistry, organ transplantation and blood transfusion.

Exposure of the UK population to BSE has been widespread with over 181,000 cases confirmed to date in cattle (5) and yet the prevalence of human infection in the UK has yet to be determined with accuracy. A retrospective study of archived surgical lymphoreticular specimens estimated a prevalence of infection in the UK of 237 per million (95% confidence interval 49-692 per million)(6), far higher than the number of vCJD clinical cases thus far with further studies failing to refine these estimates(7). The demonstration of sub-clinical carrier states of prion infection in animal models (8-10) offers a potential explanation for the discrepancy between clinical cases and supports a prevalence which is likely to be in excess of 1 in 10,000 in the UK (11).

Concern regarding secondary transmission of vCJD has had extensive effects on public health policy in the UK and elsewhere. As the clinically silent incubation period of prion infection in humans can be prolonged, potentially exceeding 50 years (12), and the prevalence is poorly defined, the extent of future transfusion-transmission of vCJD cannot be estimated or accurately risk-assessed. Secondary infection from the clinically silent population has already been confirmed in four recipients of blood transfusion (13-15). Whilst the number of transfusion recipients positively identified as having received vCJD contaminated packed red cells is small, a much larger cohort of around 7000 recipients of contaminated plasma products have already been identified and notified of their at-risk status (16). Concern for this cohort has been heightened by post-mortem evidence for infection with vCJD prions in the spleen of a person with haemophilia (11).

The infectious agents, or prions, responsible for transmission of disease are composed principally if not entirely of a misfolded form of the host prion protein, $PrP^C$. $PrP^C$ is ubiquitous, although expressed at highest levels in the central nervous system (CNS) and cells of the immune system. When recruited during prion propagation $PrP^C$ is remodelled to an aggregated, detergent insoluble isoform designated $PrP^{Sc}$ chemically identical but conformationally distinct from $PrP^C$ (17). Detection of $PrP^{Sc}$ in CNS and lymphoreticular tissues correlates widely with infection and the presence of prion infectivity (18-20) and is accepted as 100% specific for prion infection.

Although the quantities of $PrP^{Sc}$ deposited in neural tissues are sufficient during the symptomatic phase of illness for detection by conventional immunoassays such as western blotting and ELISA, levels in peripheral tissues are significantly lower (21). Quantification of infectious titre using rodent models has indicated that the levels of infectivity, and by inference $PrP^{Sc}$, in blood may be extremely low, with buffy coat fractions containing between 2-10 $LD_{50}$ Units $ml^{-1}$ during the asymptomatic phases of disease, rising to 100 $LD_{50}$ Units $ml^{-1}$ during the clinical stage (22;23).

In order to successfully identify infection in blood an assay must be able to detect PrP in a range which is several orders of magnitude below the sensitivity of conventionally employed immunoassays. Furthermore, the ratio of background $PrP^C$, which is chemically identical to $PrP^{Sc}$, is higher in blood than any other tissue and the high lipid and protein content of blood also contribute to non-specific background signals. Conventionally, immunoassays for $PrP^{Sc}$ have been dependent upon protease pre-treatment of tissues to degrade $PrP^c$ and other proteins, thereby reducing cross-reactivity (24). It has now been shown in a number of different studies that the majority of disease associated PrP may well be sensitive to proteolytic digestion with proteinase K (PK) (25-31).

The observation that prions can bind avidly to metal surfaces (32;33) has been used to develop quantitative assays for infectivity (34) that approach the high levels of sensitivity required to detect the low levels of prions and abnormal PrP associated with blood. However, prior art assays typically assess infectivity in an animal model or cell culture system which is labour intensive and time consuming as well as raising ethical issues about use of animals.

Current evidence clearly indicates there is risk of iatrogenic vCJD from transfusion of blood and purified blood components (13-15;36) and by inference from many forms of surgical and dental interventions. Taken together with the knowledge that sub-clinical carrier states of prion disease can exist (8;9) alongside protracted incubation periods for clinical disease which may span several decades (12) the implications for current and future public health are substantial. Current risk reduction strategies in the UK are extremely costly involving leucodepletion of transfused packed red cells and the sourcing of plasma from the USA based on estimates of approximately 40% of infectivity being associated with leucocytes with the remainder in plasma (37). Studies modelling the use of leucocyte depletion have demonstrated reductions in blood infectivity of between 58% (37) and 72% (38). These and related issues also apply outside the UK, for example blood donation is not permitted in the USA if the prospective donor has spent a cumulative period of 6 moths or more in Europe. This causes significant issues for US public and military blood transfusion services.

It remains a major problem that a non-invasive and specific test for prion infection is not available.

The invention seeks to overcome problem(s) associated with the prior art.

SUMMARY OF THE INVENTION

The invention provides a method for the capture and detection of abnormal PrP from whole blood or urine using a solid-state matrix. However, rather than assay this material for infectivity by transfer to cell-culture or amplify the material for visualisation by western blotting we have developed an assay for the direct immunodetection of surface-bound material, avoiding the use of any proteolytic processing to ensure the complete ensemble of abnormal PrP isoforms are available for detection.

Central to these methods are the provision of specific buffer systems for the dilution of whole blood or urine leading to the successful capture of abnormal PrP from the sample on substrate such as steel particles.

Here we present the results of applying this assay to a blind panel of 190 whole blood samples which contained 21 samples obtained from vCJD patients, 100 normal control samples obtained from National Blood Service and 69 neurological disease controls. We also present results from urine.

Provision of a blood or urine test which can identify asymptomatic patients according to the present invention provides the ability to manage the risk of transmission and allow early entry into therapeutic clinical trials.

Assay sensitivity was found to be several orders of magnitude higher than any previously reported and was able to distinguish a $10^{-10}$ dilution of exogenously spiked vCJD-infected brain from normal control brain with a significance of <0.0001. Analysis of the blind panel of 190 samples indicated the assay has a sensitivity for the detection of vCJD-infected patient blood of 71% and predicted overall specificity of approximately 99.97%.

Thus in one aspect the invention provides a method for detection of abnormal PrP in a sample of blood or urine, said method comprising:
(a) diluting the sample with buffer to comprise final concentrations of
  (i) 10 mM to 500 mM buffer agent;
  (ii) 1% to 10% w/v bovine serum albumin; and
  (iii) 1% to 8% w/v CHAPS;
(b) adding steel particles and incubating to allow PrP binding;
(c) washing the steel particles to remove diluted sample; and
(d) detecting abnormal PrP captured on the steel particles using antibody capable of binding said abnormal PrP.

Suitably step (a) comprises diluting the sample with buffer to comprise final concentrations of
(i) 50 mM to 200 mM buffer agent;
(ii) 1% to 4% w/v bovine serum albumin; and
(iii) 2% to 4% w/v CHAPS.

Suitably step (a) comprises diluting the sample with buffer to comprise final concentrations of
(i) 100 mM buffer agent;
(ii) 2% w/v bovine serum albumin; and
(iii) 2% w/v CHAPS.

In one embodiment, suitably the sample is blood and is diluted with buffer in the range 1:1 to 1:100. More suitably the blood sample is diluted with buffer in the range 1:10 to 1:100. Most suitably
the blood is from a tga20 mouse and the blood sample is diluted with buffer at 1:10; or
the blood is from a CD1 mouse and the blood sample is diluted with buffer at 1:10; or
the blood is from a hamster and the blood sample is diluted with buffer at 1:10; or
the blood is from a sheep and the blood sample is diluted with buffer at 1:100; or
the blood is from a cow and the blood sample is diluted with buffer at 1:100; or
the blood is from a human and the blood sample is diluted with buffer at 1:100.

In one embodiment, suitably the sample is urine and is diluted with buffer in the range 10:1 to 1:5. More suitably the urine sample is diluted with buffer at 1:1.

Suitably the buffer further comprises protease inhibitors.

Suitably the antibody of step (d) is selected from the group consisting of ICSM10, ICSM18, ICSM33 and ICSM35. More suitably, the sample is from a tga20 mouse and the antibody is ICSM10; or
the sample is from a CD1 mouse and the antibody is ICSM33; or
the sample is from a hamster and the antibody is ICSM18; or
the sample is from a sheep and the antibody is selected from the group consisting of ICSM10, ICSM18, ICSM33 and ICSM35; or
the sample is from a cow and the antibody is ICSM18; or
the sample is from a human and the antibody is ICSM18.

Suitably step (c) comprises washing the steel particles to remove diluted sample and subjecting the steel particles to a heat treatment for 5 minutes. More suitably, the sample is from a tga20 mouse and heat treatment is at 50 to 110 degrees Celsius; or
the sample is from a CD1 mouse and heat treatment is at 50 to 110 degrees Celsius; or
the sample is from a hamster and heat treatment is at 20 to 115 degrees Celsius; or
the sample is from a sheep and heat treatment is at 115 degrees Celsius; or
the sample is from a cow and heat treatment is at 120 degrees Celsius; or
the sample is from a human and heat treatment is at 50 to 115 degrees Celsius.

Suitably the sample is blood and the steel particles comprise AISI 304 stainless steel.

Suitably the sample is urine and the steel particles comprise AISI 316 stainless steel.

Suitably the buffer agent is Tris.

Suitably the pH is 8.4.

In another aspect, the invention relates to a dry composition comprising Tris:BSA:CHAPS in the weight ratio 1:1.65:1.65.

In another aspect, the invention relates to a solution comprising Tris:BSA:CHAPS in the molar ratio 1:0.003:0.32.

In another aspect, the invention relates to a composition as described above or a solution as described above for use in detection of abnormal PrP.

In another aspect, the invention relates to use of a composition as described above or a solution as described above for detection of abnormal PrP in a sample.

In another aspect, the invention relates to a kit comprising
(i) composition as described above or a solution as described above; and
(ii) an anti-prion antibody.

In another aspect, the invention relates to a method of aiding the diagnosis of prion infection in a subject, the method comprising
(a) providing a sample of blood or urine from said subject
(b) assaying said sample blood or urine for abnormal PrP as described above,
wherein detection of abnormal PrP indicates an increased likelihood of prion infection in the subject.

In another aspect, the invention relates to a method for detecting prion infection having sensitivity of at least 71% and specificity of at least 99.9%.

Preferred Aspects

In one preferred aspect the invention provides a method for detection of abnormal PrP in a blood sample, said method comprising:
(a) diluting the blood sample with buffer to comprise final concentrations of
 (i) 10 mM to 500 mM buffer agent;
 (ii) 1% to 10% w/v bovine serum albumin; and
 (iii) 1% to 8% w/v CHAPS;
(b) adding steel particles and incubating to allow PrP binding;
(c) washing the steel particles to remove diluted blood sample; and
(d) detecting abnormal PrP captured on the steel particles using antibody capable of binding said abnormal PrP.

Suitably step (a) comprises diluting the blood sample with buffer to comprise final concentrations of
(i) 50 mM to 200 mM buffer agent;
(ii) 1% to 4% w/v bovine serum albumin; and
(iii) 2% to 4% w/v CHAPS.

Suitably step (a) comprises diluting the blood sample with buffer to comprise final concentrations of
(i) 100 mM buffer agent;
(ii) 2% w/v bovine serum albumin; and
(iii) 2% w/v CHAPS.

Suitably the blood sample is diluted with buffer in the range 1:1 to 1:100.

Suitably the blood sample is diluted with buffer in the range 1:10 to 1:100.

Suitably the blood is from a tga20 mouse and the blood sample is diluted with buffer at 1:10; or
the blood is from a CD1 mouse and the blood sample is diluted with buffer at 1:10; or
the blood is from a hamster and the blood sample is diluted with buffer at 1:1; or
the blood is from a sheep and the blood sample is diluted with buffer at 1:100; or
the blood is from a human and the blood sample is diluted with buffer at 1:100.

Suitably the buffer further comprises protease inhibitors.

Suitably the antibody of step (d) is selected from the group consisting of ICSM10, ICSM18, ICSM33 and ICSM35.

Suitably the blood is from a tga20 mouse and the antibody is ICSM10; or
the blood is from a CD1 mouse and the antibody is ICSM33; or
the blood is from a hamster and the antibody is ICSM18; or
the blood is from a sheep and the antibody is selected from the group consisting of ICSM10, ICSM18, ICSM33 and ICSM35; or
the blood is from a human and the antibody is ICSM18.

Suitably the blood is from a human and the antibody is ICSM18.

Suitably step (c) comprises washing the steel particles to remove diluted blood sample and subjecting the steel particles to a heat treatment for 5 minutes.

Suitably the blood is from a tga20 mouse and heat treatment is at 50 to 110 degrees Celsius; or
the blood is from a CD 1 mouse and heat treatment is at 50 to 110 degrees Celsius; or
the blood is from a hamster and heat treatment is at 20 to 115 degrees Celsius; or
the blood is from a sheep and heat treatment is at 60 to 120 degrees Celsius; or
the blood is from a human and heat treatment is at 50 to 115 degrees Celsius.

Suitably the steel particles comprise AISI 304 stainless steel.

Suitably the buffer agent is Tris.

Suitably the pH is 8.4.

In another aspect, the invention relates to a dry composition comprising Tris:BSA:CHAPS in the weight ratio 1:1.65:1.65.

In another aspect, the invention relates to a solution comprising Tris:BSA:CHAPS in the molar ratio 1:0.003:0.32.

In another aspect, the invention relates to a composition as described above or a solution as described above for use in detection of abnormal PrP.

In another aspect, the invention relates to use of a composition as described above or a solution as described above for detection of abnormal PrP in a sample.

In another aspect, the invention relates to a kit comprising
 (I) composition as described above or a solution as described above; and
 (ii) an anti-prion antibody.

In another aspect, the invention relates to a method of aiding the diagnosis of prion infection in a subject, the method comprising
 (a) providing a blood sample from said subject
 (b) assaying said blood sample for abnormal PrP as described above
wherein detection of abnormal PrP indicates an increased likelihood of prion infection in the subject.

In another aspect, the invention relates to a method for detecting prion infection having sensitivity of at least 71% and specificity of at least 99.9%.

DETAILED DESCRIPTION OF THE INVENTION

The methods of the invention involve manipulation of the high avidity of abnormal PrP for metal and plastic surfaces using a solid-state matrix for capture coupled to direct immunodetection of surface bound material. Quantitative assay sensitivity was first determined using a dilution series of exogenous spikes of vCJD-infected brain into whole blood before analysing a blind panel of authentic patient blood samples. The panel comprised 190 samples, including those from vCJD and sporadic CJD patients, non-prion neurological disease controls and normal control blood samples.

An assay using a sample of blood or urine, most suitably blood, with high sensitivity and a specificity sufficient for clinical use is provided. The introduction of such a test would provide a breakthrough in the management of public health risks associated with vCJD and allow the identification of asymptomatic individuals, mitigating the risk of iatrogenic transmission and facilitating early referral for specialist care and entry into future clinical trials.

Definitions

The term 'comprises' (comprise, comprising) should be understood to have its normal meaning in the art, i.e. that the stated feature or group of features is included, but that the term does not exclude any other stated feature or group of features from also being present.

Prion Protein/PrP/PrP$^{Sc}$/PrP$^C$

The invention is concerned with the detection of prion infection or prion infectivity. More precisely, the invention in concerned with the detection of abnormal PrP or disease associated PrP. Detection of the presence of abnormal PrP or disease associated PrP is indicative of prion infection. Thus the invention is primarily concerned with the detection of abnormal PrP and the presence of abnormal PrP aids the diagnosis of prion infection in the subject being analysed. Presence of abnormal PrP may be taken as an indication of prion infection. Abnormal PrP includes $PrP^{Sc}$ within the complete ensemble of abnormal PrP isoforms; thus abnormal PrP comprises $PrP^{Sc}$. Most suitably the abnormal PrP may be $PrP^{Sc}$.

The abnormal PrP detected may be quantified. Quantities of abnormal PrP detected may be expressed as masses, or as equivalents of $LD_{50}$ Units of infectivity.

An exemplary or reference sequence for human PrP is given in SEQ ID NO: 7.

Sample

The sample may be blood or urine. For convenience, the assay is mostly described in relation to blood. However, unless otherwise indicated, the disclosures herein may be applied equally to the assay whether the sample is blood or is urine. Regarding two specific factors (dilution and steel type) there may be advantages to using a specific condition when the sample is blood and a different specific condition when the sample is urine. For example, although all of the steels used herein may be applied to blood or to urine, there is an advantage to using steel AISI 304 when the sample is blood and there is an advantage to using steel AISI 316 when the sample is urine. Thus it can be appreciated that the disclosure provided is applied equally to blood or to urine, except where specifically mentioned otherwise.

It is a key advantage of the invention that detection of abnormal PrP in a sample of blood or urine, most suitably blood, is disclosed. In particular this is accomplished whilst avoiding protease treatment. In particular this is accomplished whilst avoiding immunoprecipitation steps. Thus suitably the sample analysed comprises blood or urine, most suitably blood.

The sample may be from a subject. The subject is suitably a mammal, most suitably a livestock animal or a human, most suitably a human.

The sample of blood or urine, most suitably blood may be collected as a preliminary step of the method of the invention. More suitably the method of the invention begins with a sample of blood or urine, most suitably blood previously collected so that collection of the sample is suitably not a part of the invention. This has the advantage that the subject need not be present for the methods of the invention.

Suitably the sample of blood or urine, most suitably blood is diluted for detection. Dilution of the sample is very important to the invention. The capture buffer has been carefully developed for diluting the sample to provide excellent results. Dilution of the sample over particular ranges is important to signal generation.

Blood Dilution

Typically blood is diluted 1:1 to 1:100. Most suitably the optimal dilution is chosen according to the species as in the following table:

| | Blood Dilution (all or nothing response) | | |
|---|---|---|---|
| Species | Low | High | Functional |
| Mouse (tga20) | 1:1 | 1:100 | 1:10 |
| Mouse (CD1) | 1:1 | 1:100 | 1:10 |
| Hamster | 1:1 | 1:100 | 1:1 |
| Sheep | 1:1 | 1:100 | 1:100 |
| Human | 1:1 | 1:10,000 | 1:100 |
| Cow | 1:1 | 1:100 | 1:100 |

For species not listed in the table, the skilled worker can determine the optimal dilution by trial and error using the given values as a start point. In example 5 there is provided a protocol for determination of optimised dilutions.

The volume of blood required may be chosen by the operator according to the volume(s) available and the processing requirements. A typical volume used is 8 μl of whole blood per aliquot/sample.

Without wishing to be bound by theory, the actual volume used is not thought to be critical. For example, doubling the volume used does not necessarily double the signal detected—the dilution of the blood is more important as explained above.

Blood derivatives such as blood fractions may be used in place of blood. For example, the red cell fraction may be used, the mononucleocyte fraction may be used, or the plasma fraction may be used. Typically such blood fractions perform in the method of the invention, but whole blood is preferred since it typically provides a stronger signal than blood fractions.

Urine Dilution

In contrast to blood, higher dilutions of urine such as 1:100 do not typically give robust signal for urine.

Typically urine is diluted 10:1 to 1:5. More suitably urine is diluted 2:1 to 1:2. Most suitably the optimal dilution of urine is 1:1.

If necessary, the skilled worker can determine the optimal dilution by trial and error using the given values as a start point. In example 5 there is provided a protocol for determination of optimised dilutions.

The volume of urine required may be chosen by the operator according to the volume(s) available and the processing requirements. A typical volume used is 400 μl of whole urine per aliquot/sample.

Without wishing to be bound by theory, the actual volume used is not thought to be critical. For example, doubling the volume used does not necessarily double the signal detected—the dilution of the sample is more important as explained above.

When the sample comprises urine, most suitably the urine is human urine.

Diagnosis

The invention provides methods for aiding the diagnosis of prion infection. Such methods are suitably performed on an isolated sample from the subject being investigated. Thus, suitably the methods are methods which may be conducted in a laboratory setting without the need for the subject to be present. Suitably the methods are carried out in vitro i.e. suitably the methods are in vitro methods. Suitably the samples are in vitro i.e. suitably the samples are in vitro samples.

Capture

According to the invention, abnormal PrP is captured on steel particles. The inventors have found that specific form(s) and/or amount(s) of steel particles can provide advantageously good results.

Suitably the steel particles used comprise steel powder.

Suitably the steel used is an austenitic stainless steel.

Suitably the steel used is a '3-series' austenitic steel.

Suitably the steel used comprises AISI 316 or AISI 304; most suitably the steel used comprises AISI 304.

Suitably when the sample is blood the steel particles comprise AISI 304 stainless steel.

Suitably when the sample is urine the steel particles comprise AISI 316 stainless steel.

AISI is an international standard for the composition of steel. AISI 304 and AISI 316 are austenitic stainless steels with the chemical compositions:

AISI 304 chemical composition: C=0.08% max, Mn=2% max, Cr=19%, Ni=9.5%

AISI 316 chemical composition: C=0.08% max, Mn=2% max, Cr=17%, Ni=12%, Mo=2.5%

Steels of these compositions from any manufacturers/suppliers may be used in the invention.

Most suitably steel is obtained from the commercial supplier Goodfellow.

Steel can be used within a concentration range of 5 mg to 90 mg ml$^{-1}$. It is most effective in the range 10 to 50 mg ml$^{-1}$ and is optimal at 23 mg ml$^{-1}$.

The assay performance can be improved by preparing the steel before use. Suitably the steel is prepared by washing in aqueous detergent solution followed by washing in water, and then washing in an aqueous alcohol solution followed by washing in water. Finally the steel particles may be resuspended in phosphate buffered saline (PBS) ready for use.

An exemplary preparation method is as follows:

Prepare stock solution of 100 mg/ml of new batch of steel powder (AISI 304). Wash approximately 3 g in 30 ml 2% triton-x-100 (sigma)/sterile ddH2O in a falcon tube for 2 hours at room temperature. Remove liquid and wash powder 5×10 mins in 30 ml sterile ddH2O on rocking platform. Wash steel in 30 ml 70% ethanol and incubate for 10 mins on rocking platform, then wash again in 3×30 ml sterile ddH2O. Remove small aliquots of 1 ml into eppendorf tubes. Remove all liquid and weigh powder. Resuspend in PBS to give a final concentration of 100 mg/ml powder, aliquot into replica eppendorf tubes giving final mass of steel powder of 23 mg (230 µl of 100 mg/ml stock), then remove all liquid.

Suitably prepared steel particles are not allowed to dry out before use. Suitably steel particles are used within about 4 days of preparation.

Capture Buffer

The capture buffer comprises three core elements—detergent, buffer agent and background protein. The capture buffer may also contain one or more optional elements as discussed below.

Without wishing to be bound by theory, the buffer described herein have been arrived at to provide an advantageous balance between the need to disrupt membranes and release PrP, but without being so stringent as to disrupt PrP conformation and/or binding to steel.

Suitably chaotropic agents such as guanidine are not used. Without wishing to be bound by theory, it is believed that guanidinium is ineffective, which may be due to the chaotropic action releasing bound material from the steel surface. Suitably chaotropic agents such as guanidine are omitted from the methods and compositions of the invention.

Concentrations referred to are FINAL concentrations in use. This means final concentrations when diluted with the sample of blood or urine, most suitably blood to form the sample being analysed. Most typically a stock solution of capture buffer is prepared having correspondingly higher concentrations of the constituents so that when it is combined with sample of blood or urine, most suitably blood the concentrations are the final concentrations. For the avoidance of doubt, the concentrations being discussed are FINAL concentrations (i.e. concentrations when diluted with sample of blood or urine, most suitably blood) unless otherwise specified.

Detergent

The detergent is suitably a mild detergent such as a detergent suitable for use in NMR.

Suitably the detergent is a weak zwitterionic detergent. Suitably the detergent may be selected from any similar class of detergent such as sulphobetaine in any of its forms (3-06, 3-08, 3-10, 3-12, 3-14, 3-16), alkyldimethylamine oxides, alkyl glucosides, alkyl maltosides, alkyl sulphates, alkyl thioglucosides, Big CHAPS, CHAPSO, Bile acids, digitonin, glucamides, lecithins, lysolecithins, polyoxyethylenes or quaternary ammonium compounds such as CTAB.

The detergent is suitably CHAPS (3-[(3-cholamidopropyl)dimethylammonio]-1-propanesulfonate).

CHAPS is suitably used at between 1% and 8% w/v, being effective at these concentrations.

More suitably CHAPS is used at between 2% and 4% which has the advantage of working most effectively.

Most suitably CHAPS is used at 2%, which has the advantage of being optimal.

Buffering

The capture buffer may comprise buffer agent such as tris(hydroxymethyl)aminomethane (Tris) e.g. Tris.Cl or alternative buffer. In principle it is expected that any buffer would be functional. Phosphate buffered saline (PBS) may be used but Tris buffer offers improved performance relative to PBS. Suitably the buffer agent comprises Tris e.g Tris.Cl.

Suitably the buffer agent is used at a concentration of 10 to 500 mM.

More suitably the buffer agent is used at a concentration of between 50 and 200 mM, which has the advantage of producing best results.

When calculating the concentration of, or how to prepare, the buffer agent such as Tris, account must be taken of the molecular weight and/or the salt used. For example Tris has a molecular weight of 121.14, but is often supplied as Tris.Cl/Tris.HCl, and so molecular weights must be taken into account in preparation of the final concentration desired. For example 1 g of Tris may need to be adjusted to 1.3 g if using Tris.HCl (since Tris.HCl has a molecular weight of 157.56). Such adjustments are well within the abilities of the person skilled in the art. Unless otherwise indicated, weights given are for Tris.

The buffer is suitably pH 8.4.

Protein

Background protein is included in the capture buffer.

Suitably the background protein is Bovine Serum Albumin (BSA). Suitably this is used between 1% and 10% w/v.

More suitably this is used between 1 and 4%, which has the advantage of operating best.

Most suitably this is used at 2%, which has the advantage of being optimal.

Protease Inhibitors

Optionally protease inhibitors such as commercially available 'Complete Inhibitors' are included in the capture buffer. Most suitably the protease inhibitors are 'Roche Complete protease inhibitor cocktails tablets' (Roche Diagnostics GmbH) and are used according to the manufacturer's instructions. This has the advantage of eliminating protease treatments which have formed part of prior art methods. This also has the technical advantage of preserving more abnormal PrP signal. It is believed that some abnormal PrP types are in fact susceptible to protease degradation. Therefore the invention advantageously specifically excludes protease treatment. Suitably the invention relates to methods from which protease step(s) are omitted. Suitably the methods of the invention comprise inhibition of protease activity.

Nuclease

Optionally nuclease such as commercially available 'Benzonase' is included in the capture buffer.

Chelator

Optionally a chelator such as EDTA may be included in the capture buffer.

DMSO

Abnormal PrP may be aggregated into fibrillar structures. A solvent for amyloid is dimethyl sulphoxide (DMSO) and this may optionally be used as a pre-treatment for samples such as blood samples.

Thus, optionally a DMSO pretreatment may be applied to the sample before dilution into capture buffer. When optional DMSO pretreatment is used, it does not affect the final dilution ratio into capture buffer. When used, optional DMSO pretreatment can be considered as the first step in a two stage dilution. For example, if a final dilution of 1:100 is desired and an optional DMSO pretreatment is used, then a first step of 1:10 with DMSO may be used followed by a second step 1:10 into a final concentration of capture buffer may be used.

When used, it is desired to dilute the sample with DMSO first, and then secondly dilute into capture buffer. Simply adding DMSO to capture buffer with the sample in a one-step procedure is not desired.

Thus, when used, the dilution step can be carried out as two sub-steps (a-1) adding DMSO to sample (a-2) diluting DMSO-sample with buffer to comprise final concentrations as described.

For example 8 ul of blood can be diluted to 80 ul in 50% v/v DMSO in PBS. This is optionally incubated at room temperature (21 C) for 4 hours with agitation. The samples are then diluted to final volume of 800 ul in DDA capture buffer containing 15% v/v DMSO. The assay can then be performed as described.

Stock Solutions of Capture Buffer

As noted above, higher concentrations of buffer may be prepared for use as stock solutions in order to ease preparation of blood/urine dilutions.

For example a final concentration of 100 mM Tris, 2% BSA, 2% CHAPS may be desired and a 5× stock may be prepared which would comprise 500 mM Tris, 10% BSA, 10% CHAPS. Thus the invention relates to buffers having these components in fixed ratios, independent of their precise concentrations. These have the advantage of facilitating dilutions and sample preparation. Thus for example compositions comprising this molar ratio, whether they be a 1×, 2× or any other concentration are provided by the invention.

| Solutions | | | | |
|---|---|---|---|---|
| Component | Functional | Amount Advantageous | Optimal | Optimal molar ratio |
| Buffer agent (e.g. Tris) | 10 to 500 mM | 50 to 200 mM | 100 mM | 1 |
| BSA | 1% (150 μM) to 10% (1.5 mM) | 1% (150 μM) to 4% (600 μM) | 2% (300 μM) | 0.003 |
| CHAPS | 1% (16 mM) to 8% (130 mM) | 2% (32 mM) to 4% (65 mM) | 2% (32 mM) | 0.32 |

| Dry Compositions | | | |
|---|---|---|---|
| | | Amount (to make 1 litre solution) | |
| Component | Functional | Advantageous | Optimal |
| Buffer agent (e.g. Tris MWt 121.14) | 1.21 g to 60.6 g | 6.06 g to 24.23 g | 12.1 g |
| BSA | 10 g to 100 g | 10 g to 40 g | 20 g |
| CHAPS | 10 g to 80 g | 20 g to 40 g | 20 g |

| Dry Ratios | | | |
|---|---|---|---|
| Component | Functional | Ratio Advantageous | Optimal |
| Buffer agent (e.g. Tris MWt 121.14) | 1 | 1 | 1 |
| BSA | 0.17 to 83 | 0.41 to 6.6 | 1.65 |
| CHAPS | 0.17 to 66 | 0.83 to 6.6 | 1.65 |

Heat Treatment

A heat treatment is optionally applied to the steel particles after washing and before detection. This has advantage of exposing ('retrieving') epitopes on the captured PrP and thereby making it more amenable to detection by antibody.

It is possible that a chemical treatment could be used to expose epitopes on the captured PrP. However, guanidinium is ineffective, which may be due to the chaotropic action releasing bound material from the steel surface. Therefore it is preferred that the optional exposing/retrieving epitopes step is performed as a heat treatment.

The duration of the heat treatment is typically 5 minutes.

The heat treatment may be applied by any suitable means known in the art such as by water bath (for temperatures up to 100 degrees Celsius), oil bath, heating block, or any other device.

The heat treatment may be optimised depending on the species of PrP being detected (i.e. the species from which the sample of blood or urine, most suitably blood is derived). The table below provides exemplary values. Values for species not listed may be determined by trial and error using these values as a start point.

| | Temperature (not essential, provides enhancement) | | |
|---|---|---|---|
| Species | Low | High | Optimal |
| Mouse (tga20) | 50 | 110 | 110 |
| Mouse (CD1) | 50 | 110 | 65 |
| Hamster | 20 | 115 | 20 |
| Sheep | 60 | 120 | 120 |
| Human | 50 | 115 | 110 |
| Cow | 90 | 120 | 120 |

Detection

Detection of the actual abnormal PrP captured on the steel particles can in principle be carried out by any suitable method known in the art.

The term 'antibody' should be understood to be an especially suitable reagent or embodiment—it must be noted that antibody fragments, sc-Fv, fused or humanised antibodies or other antibody-derived reagents or affybodies or aptamer-type binding reagents may be used if desired. The important element is to have a reagent which can selectively, specifically bind abnormal PrP so that the presence or absence or abnormal PrP can be read out from the steel particles.

Thus the precise mode of detection of the abnormal PrP bound to the steel particles is a matter for the skilled worker. An exemplary approach is to contact the steel particles with a primary antibody capable of binding abnormal PrP, and incubating to allow binding. Excess antibody is then washed away. Binding of this primary antibody may then be detected e.g. by use of secondary antibody with chemiluminescence or similar.

Suitably the primary antibody is biotinylated which allows any avidin-based secondary reagent to be used for detection. However, if desired the primary antibody may equally be conjugated to an enzyme for detection such as horseradish peroxidise (HRP) or other well known moiety.

In a preferred embodiment detection is by application of one or more of the primary antibodies ICSM10, ICSM18, ICSM33 or ICSM35 to the steel particles. The ICSM antibodies are publicly availably e.g. from D-Gen Ltd (UK).

Suitably the antibody or antibody derived detection reagent comprises CDRs of ICSM10, ICSM18, ICSM33, or ICSM35 as appropriate. I.E. suitably the antibody or antibody derived detection reagent comprises CDR amino acid sequence as shown herein.

A designation of "B" following an antibody indicates that it is biotinylated. For example, ICSM10B means ICSM10 biotinylated antibody.

ICSM10 (D-Gen Product No. 0130-01001) is a monoclonal anti-prion protein (PrP); purified mouse immunoglobulin. The antibody isotype is IgG1 K. ICSM10 specifically reacts with human native and denatured PrPC and denatured PrPSc. The antibody also reacts with sheep, mouse, hamster and bovine PrP. By Western blotting and immunoprecipitation ICSM 10 does not bind to diglycosylated PrP; binding only un-glycosylated PrP and a subset of mono-glycosylated PrP. The mono-glycosylated PrP detected by ICSM 10 has a higher relative molecular mass than detected by ICSM 3 (Beringue et al., 2003 for mouse PrP).

The detection reagent of the present invention may comprise one or more antibodies or antibody fragments capable of binding abnormal PrP, mimetics thereof or small molecule(s) capable of binding abnormal PrP or combinations thereof. Preferably the detection reagent of the invention is an antibody or fragment thereof, preferably a monoclonal antibody or fragment thereof. Preferably the agent of the invention comprises an antibody or antibody fragment capable of binding abnormal PrP, such as ICSM10, ICSM18, ICSM33 or ICSM35 antibody or a fragment thereof.

Suitably the antibody comprises at least the CDRs of one or more antibodies shown in the sequence listing.

Advantageously when the agent is an antibody, said antibody is a humanised antibody. Humanisation of antibodies is well known in the art and can be easily accomplished by the skilled worker. For example, an antibody may be humanised with reference to the sequences encoding the CDRs presented herein. In this regard, SEQ ID NO: 1 corresponds to ICSM35VH;
SEQ ID NO: 2 corresponds to ICSM35VK;
SEQ ID NO: 3 corresponds to ICSM18VH;
SEQ ID NO: 4 corresponds to ICSM18Ic.
SEQ ID NO: 5 corresponds to ICSM33 VH.
SEQ ID NO: 6 corresponds to ICSM33 VK.

Moreover, reference is made to FIG. 4 to FIG. 8B, which show the CDR and other key sequences for exemplary antibodies.

Guidance regarding humanisation may be found for example in the literature as published by Greg Winter et al., and techniques for the manipulation and production of recombinant antibodies may be found in Harlow and Lane 'Antibodies-A Laboratory Manual', Cold Spring Harbour press.

In one embodiment, the antibodies (or fragments) may advantageously be humanised by manufacture of chimaeric antibodies.

In another embodiment, the antibodies (or fragments) may advantageously be CDR-grafted.

In another embodiment, the antibodies (or fragments) may advantageously be fully humanised to the extent that the technology permits.

In a preferred embodiment this primary antibody is biotinylated. More preferably, this is deliberately over-biotinylated e.g. to approximately 14× (i.e. approx 14 biotins per antibody molecule). This may be easily accomplished by conventional biotinylation but using approx. 10× the usual amount of biotin precursor/biotin reagent.

The invention may be applied to any species susceptible to prion infection. For example the invention may also be applied to bovine species such as dairy or beef cattle; capreoline species such as Capreolus or Cervidae (e.g. elk or venison deer); or any of the species in the tables herein.

Especially advantageous primary antibodies for detection of abnormal PrP for particular species are shown in the following table. Others may be selected by trial and error with reference to the examples section.

| | Antibody | | |
|---|---|---|---|
| Species | Functional | Non-Functional | Optimal |
| Mouse (tga20) | ICSM10 | ICSM18, ICSM33, ICSM35 | ICSM10 |
| Mouse (CD1) | ICSM33 | ICSM10, ICSM18, ICSM35 | ICSM33 |
| Hamster | Not determined | Not determined | ICSM18 |
| Sheep | ICSM10, ICSM18, ICSM33, ICSM35 | None | ICSM33 |
| Human | ICSM18 | ICSM10, ICSM33, ICSM35 | ICSM18 |
| Cow | ICSM18, ICSM35 | ICSM10, ICSM33 | ICSM18 |

In more detail, method for detection of abnormal PrP in a sample of blood or urine, most suitably blood may be carried out as follows:

(a) diluting the sample of blood or urine, most suitably blood with buffer to comprise final concentrations of
  (i) 10 mM to 500 mM buffer agent;
  (ii) 1% to 10% w/v bovine serum albumin; and
  (iii) 1% to 8% w/v CHAPS.
(b-i) adding steel particles
  Optionally the steel particles may be prepared as follows:
    Prepare stock solution of 100 mg/ml of new batch of steel powder (AISI 304). Wash approximately 3 g in 30 ml 2% triton-x-100 (sigma)/sterile ddH2O in a falcon tube for 2 hours at room temperature. Remove liquid and wash powder 5×10 mins in 30 ml sterile ddH$_2$O on rocking platform. Wash steel in 30 ml 70% ethanol and incubate for 10 mins on rocking platform, then wash again in 3×30 ml sterile ddH$_2$O. Remove small aliquots of 1 ml into eppendorf tubes. Remove all liquid and weigh powder. Resuspend in PBS to give a final concentration of 100 mg/ml powder, aliquot into replica eppendorf tubes giving final mass of steel powder of 23 mg (230 µl of 100 mg/ml stock), then remove all liquid.

Ideally the 23 mg 'dry' steel particle aliquot is combined with a final volume of sample (blood-buffer or urine-buffer mix) of 800 µl.

In practice the 23 mg steel has a 'dry' volume of approx. 25 µl. Thus in practice the total volume of the sample (blood-buffer or urine-buffer mix) with the steel added is approx. 825 µl. It should be noted that 'dry' means merely that the excess liquid has been removed; it does not infer that the prepared steel is dried; in fact it is better to avoid the drying of the prepared steel, for example by drawing off the liquid just before adding the sample or by covering the steel (e.g. by placing a lid on the container) after the liquid has been drawn off so that it does not dry out.

(b-ii) incubating to allow PrP binding

This may be done by incubating the steel powder with each sample for at 18° C. o/n at 650 rpm on a thermomixer.

(c) washing the steel particles to remove diluted sample;

This washing procedure may be done by capturing steel powder samples with magnetic block and removing supernatant; washing steel powder samples 2×1 ml PBS/0.05% tween capturing each time on magnetic block. Vortex samples in wash buffer and spin briefly. Wash a further 3×1 ml PBS/0.05% tween capturing each time on magnetic block. Spin samples briefly and remove all liquid.

At this stage, an optional heat treatment may be used to improve detection. If used, the heat treatment step may be carried out as follows: Heat treat all samples of steel powder at appropriate temperature (see table) for 5 minutes on a heat block. Allow samples to cool for 3 minutes.

(d) detecting abnormal PrP captured on the steel particles using antibody capable of binding said abnormal PrP.

The detection step may be accomplished by any suitable method known in the art. For example, it may be carried out as follows: incubate steel powder samples with 50 µl of detection reagent such as primary antibody capable of binding abnormal PrP (e.g. with an appropriate ICSM antibody-see table) prepared in PBS/1% tween at 1 µg/ml; for 1 hour at 37° C. and 750 rpm on a thermomixer; wash steel powder samples 1×1 ml PBS/0.05% tween capturing each time on magnetic block. Add 1 ml PBS/0.05% tween then vortex samples in wash buffer and spin briefly. Remove buffer and wash a further 1×1 ml PBS/0.05% tween capturing each time on magnetic block. Spin briefly and remove all liquid. Incubate steel powder samples with 50 µl of Neutravidin-HRP (Pierce) prepared in PBS/1% tween at 1:100,000 for 45 minutes at 37° C. and 750 rpm on a thermomixer. Prepare a serial dilution series of secondary detection reagent such as secondary antibody (1:100,000, 1:1 million and 1:10 million). Wash steel powder samples 1×1 ml PBS/0.05% tween capturing each time on magnetic block. Add 1 ml PBS/0.05% tween then vortex samples in wash buffer and spin briefly. Remove buffer and wash a further 1 × 1 ml PBS/0.05% tween capturing each time on magnetic block. Mix equal volumes of Supersignal ELISA femto chemiluminescent substrate (Thermo Scientific). Add 60µl of chemiluminescent substrate to steel powder aliquots, mix thoroughly by pipetting and aliquot into 3×200 in 3 replica wells of black ELISA plates (Greiner). To 2 replica wells add 20 µl of each dilution of the secondary antibody dilution series. Add a further 80 µl per well of Supersignal ELISA femto chemiluminescent substrate. Place plate into Tecan M1000 plate reader immediately. Shake for 60 seconds on plate reader then read plate on luminescence, attenuation automatic settings.

Combinations

The methods of the invention may advantageously be combined e.g. with tonsil biopsy and/or with MRI scan. For example if a subject is indicated as having an increased likelihood of infection by a method of the invention, then it may be desired to perform a tonsil biopsy and/or MRI scan in order to confirm the diagnosis.

Application to Urine

The assay steps when urine is the sample are the same as the assay steps when blood is the sample. The only difference is the dilution. Details are given for preferred blood dilutions and preferred urine dilutions separately herein. There are also advantages to different steels for blood and for urine, although each of the steels disclosed herein works with both sample types.

To the knowledge of the inventors, abnormal PrP has never been detected in urine before the present invention.

Numerous commercial hormone products are prepared (purified) from urine. Therefore testing of urine is commercially desirable. For example, in Canada approx. 300,000 patients per year receive hormone products purified from urine. This is a further clear industrial application for the invention when the sample is urine.

Industrial Application

The invention provides a blood or urine, most suitably blood, based assay for the detection of prion infection such as vCJD prion infection.

The invention finds application in aiding clinical diagnostic testing in cases of neurological disease where prion disease forms part of the differential diagnosis.

The methods of the invention may be used in a high throughput format for example for use by the UK National Blood Service and/or other similar international agencies.

The invention finds application in pre-surgical screening of patients to reduce or eliminate the risk of contaminating instruments and medical devices with vCJD prions.

The invention may be applied to screening of tissue and/or organ donations.

The invention may be used for detection of various strains/species of prion disease for elimination from the human food chain, eg Chronic Wasting Disease, BSE, sheep scrapie.

The methods disclosed may be used in prevalence screening for vCJD in humans and BSE, CWD and scrapie in animals.

The invention can be used to assist in eradicating animal prion diseases in commercial herds. The invention may be applied to the testing of commercial herds such as of cattle and sheep.

The invention provides a laboratory based test to replace rodent bioassay in many areas of prion research where they are used for sensitivity.

BRIEF DESCRIPTION OF THE FIGURES

FIG. 4 to FIG. 8B show annotated antibody sequences. Note: boxed residues are CDRs: unboxed, bold residues are the start of the constant region; regions which are neither leader sequence, constant region nor CDR are defined as framework sequence. FIG. 4 presents the amino acid sequences of ICM33VH (SEQ ID NO: 5) and ICM33VK (SEQ ID NO: 6). FIG. 5 shows the DNA and amino acid sequences of ICSM35VH (SEQ ID NO:1 and NO:8, respectively). FIG. 6 shows the DNA and amino acid sequences of ICSM35VK (SEQ ID NO:2 and NO:9, respectively). FIG. 7 presents the DNA and amino acid sequences of ICSM18VH (SEQ ID NO:3 and NO:10, respectively). FIG. 8A presents the DNA and amino acid sequences and FIG. 8B shows the DNA sequence of ICSM181c (SEQ ID NO:4 and NO:11, respectively).

FIG. 9 shows data from sheep.

FIG. 10 shows data from cows.

Figure 1:
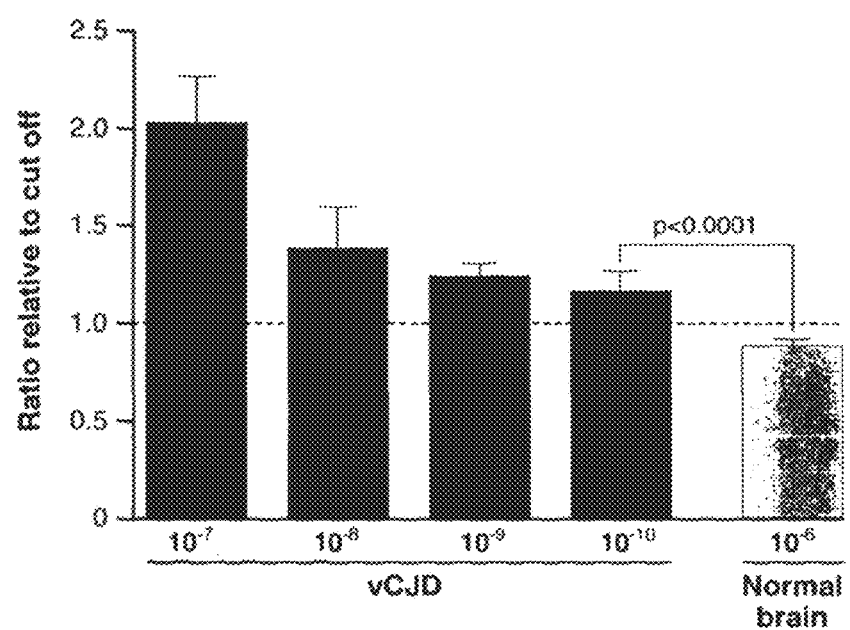
FIG. 1 shows assay sensitivity to exogenous spiked samples: A serial dilution of vCJD-infected brain homogenate was prepared in whole human blood. A baseline control of a high concentration of normal human brain ($10^6$-fold dilution) in whole human blood was used to establish a cut-off threshold. Dilutions of up to $10^{-10}$ of vCJD-infected brain exogenously spiked into whole human blood could be detected at a signal level over three standard deviations above the mean value for a normal brain spike. Data shown is a mean of six replicates and is expressed as a ratio relative to the cut-off value (dashed line). The two tailed p value for comparison of $10^{-10}$ vCJD and $10^{-6}$ normal brain signals is <0.0001 (unpaired t test with Welch correction).

The invention is now described by way of example. These examples are intended to be illustrative, and are not intended to limit the appended claims.

EXAMPLES

Methods
Collection and Storage of Human Blood Samples

These studies were approved by the local research ethics committee of University College London Institute of Neurology and National Hospital for Neurology and Neurosurgery. Blood samples were obtained with consent, collected in EDTA blood tubes and stored frozen at −70° C. Diagnosis of vCJD was made according to established criteria e.g. http://www.advisorybodies.doh.gov.uk/acdp/tseguidance/tseguidance_annexb.pdf.Definite sporadic CJD was diagnosed according to WHO criteria and diagnosis of probable sporadic CJD according to published WHO criteria with a high specificity (35). Normal control blood was obtained as EDTA samples from the National Blood Service of England and Wales (NBS).

Assaying Blood Spiked with vCJD and Normal Brain Homogenate:

Steel particles (AISI 304; Goodfellow) were prepared by washing in 2% v/v Triton-X-100 in ddH$_2$O for 2 hours at room temperature. Steel was captured with a magnet and washed 5× with an excess of ddH$_2$O and sterilised by washing in 70% v/v ethanol before washing again with an excess of ddH$_2$O. Aliquots of 23 mg were removed to microfuge tubes, captured with a magnet and the liquid aspirated with a pipette. 5 µl of 10% w/v vCJD-infected brain homogenate or normal human brain homogenate was spiked into 9995 µl of whole human blood. From this a serial dilution series of $10^{-7}$ to $10^{-10}$ of vCJD-infected brain homogenate into whole human blood was prepared. Each sample was further diluted 2 fold into capture buffer [200 mM Tris pH 8.4, 4% w/v BSA, 4% w/v CHAPS, 2× Complete protease inhibitors (Roche), 80 Units Benzonase (GradeII, Merck)] for assay. To each aliquot of steel powder, 800 µl of spiked blood/buffer mix was added and incubated at 18° C. with agitation overnight.

Steel was captured on a magnetic rack and the supernatant discarded. Steel was washed 5× with 1 ml PBS+0.05% v/v Tween-20 (PBST). After the final wash all liquid was removed and the steel heat treated at 115° C. for 5 minutes. To each tube an aliquot of 50 µl of biotinylated primary antibody ICSM18 (D-Gen, Ltd) prepared at 1 µg/ml in PBS+1% v/v Tween-20 was added and incubated at 37° C. with agitation for 1 hour. Samples were washed 3× with 1 ml PBST capturing between washes on a magnetic rack. Each sample was then incubated with High Sensitivity NeutrAvidin-HRP (Pierce) prepared at a 1:100,000 dilution in PBS+1% v/v Tween-20 at 37° C. with agitation for 45 minutes.

Finally samples were washed 3× with 1 ml PBST capturing between washes on a magnetic rack. To each sample 60 µl of SuperSignal ELISA Femto chemiluminescent substrate (Pierce) was added and 20 µl of each steel powder sample was transferred into 3 replica wells of a black flat bottom ELISA plate (Greiner). Immediately prior to reading the plate a further 80 µl of SuperSignal ELISA Femto chemiluminescent substrate was added per well. A dilution series of 1:100,000 to 1:10 million of the High sensitivity NeutrAvidin-HRP (Pierce) was prepared to allow for correction in absolute chemiluminescent readings across multiple plates. Plates were scanned using a M1000 plate reader (Tecan).

Assaying of Patient Blood Samples:

Steel particles (AISI 304; Goodfellow) were prepared as detailed above. To each aliquot of steel, 800 µl of a 1:100 dilution of whole human blood into capture buffer (as above) was added and incubated at 18° C. with agitation overnight. Steel was captured on a magnetic rack and the supernatant discarded before processing as described above. Plates were scanned using a M1000 plate reader (Tecan) in chemiluminescence mode.

The Blind Panel and Scoring of Samples:

A panel of 190 whole blood samples comprising 21 from vCJD patients, 100 normal controls (provided by the NBS), 16 patients with probable sCJD, 11 confirmed sCJD cases as well as 69 samples from other neurodegenerative diseases (25 Alzheimer's Disease, 4 Frontal Temporal Dementia (FTD), 6 Familial Alzheimer's Disease (FAD) and 7 neurological referrals to the National Prion Clinic confirmed as not Prion Disease) were prepared as blind samples numbered 1 to 190 by parties independent of the assay and analysis. Each of the blind panel samples were tested twice in independent assays as described above. Samples were processed and analysed in groups of 19 blind panel samples per 96-well plate with a set of 8 quality control samples containing 6 normal control blood samples and 2 vCJD-infected patient blood samples.

Samples were scored as reactive if the ratio of the mean chemiluminescence signal from three replicate wells exceeded a cut-off threshold determined for each plate. The threshold was set at the mean plus 3×Standard Deviations from the mean of the 6 normal blood samples on each plate. Thus samples with a ratio of greater than 1 were considered reactive. Samples that were reactive in each of the two independent assays were scored as positive samples. On completion of testing all samples in duplicate the results were declared to an independent party and the samples decoded.

Example 1

Detection of vCJD Brain Homogenate Spiked into Whole Blood

In order to determine the sensitivity of the assay relative to other methods we analysed serial dilutions of vCJD brain homogenate diluted into whole blood to provide a background diluent as close to endogenous patient samples as possible. A dilution range of $10^{-7}$ to $10^{-10}$ of 10% w/v vCJD brain homogenate was assayed and compared to a high background concentration ($10^{-6}$) of normal brain homogenate (10% w/v) also diluted in whole blood. Although a non-linear response was seen with respect to dilution, vCJD-infected brain homogenate could clearly be distinguished from control even at a $10^{-10}$ fold dilution (FIG. 1), a sensitivity more than 4 logs higher than previously achieved for immunoassay of vCJD tissue (31). A chemiluminescent signal of $1.3 \times 10^5 +/- 1.1 \times 10^4$ (mean+/−SD) was obtained with $10^{-10}$ dilution of vCJD-infected brain versus $9.9 \times 10^4 +/- 4.5 \times 10^3$ for a $10^{-6}$ dilution of normal control brain. Data is expressed as a ratio relative to cut off (see Materials and Methods) this was 1.17+/−0.1 (mean+/−SD). The difference was highly significant with a p value of $\leq 0.0001$ (unpaired t-test, two-tailed with Welch correction). The highest dilution of vCJD brain was still distinguishable from the normal control when a threshold of mean normal signals+3×standard deviations was applied.

Example 2

Identification of vCJD Infected Patient Bloods

Figure 2:
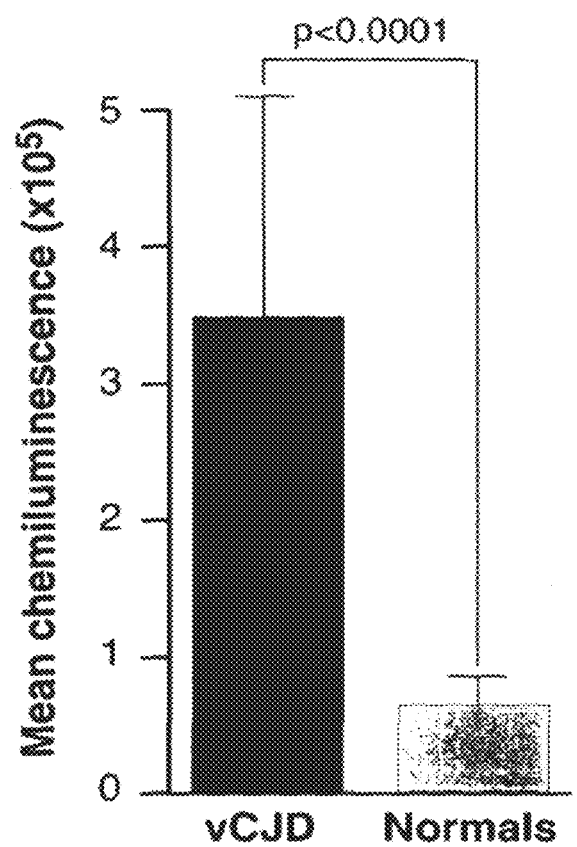
FIG. 2 shows discrimination of endogenous vCJD patient blood from normal controls: Data shown are the mean chemiluminescent signal (arbitrary units) of 14 blood samples from unique, confirmed vCJD patients compared to the mean signal from 100 normal controls. Error bars represent the standard deviation from the mean signals. The two tailed p value for comparison of vCJD and normal blood samples is <0.0001 (unpaired t test with Welch correction).

Initial studies performed using exogenous spikes of vCJD-infected brain homogenate in whole human blood demonstrated our assay was capable of discriminating between infected and non-infected samples with a sensitivity theoretically sufficient to detect infection in vCJD blood based upon estimates of titre obtained from rodent models (22;23). However, the biochemical nature of infectivity and abnormal PrP associated with blood is unknown and the results obtained from exogenous spiking experiments cannot be assumed to apply to authentic patient samples. To ensure this level of discrimination could be achieved with endogenous blood samples we tested a sub-set of confirmed vCJD patient bloods obtained from the National Prion Clinic and compared these to normal control bloods obtained from the NBS (FIG. 2). The samples were analysed as groups which had mean chemiluminescent signals that were significantly different (p value<0.0001, unpaired t-test, two-tailed with Welch correction).

Example 3

Blind Panel Analysis

Figure 3:
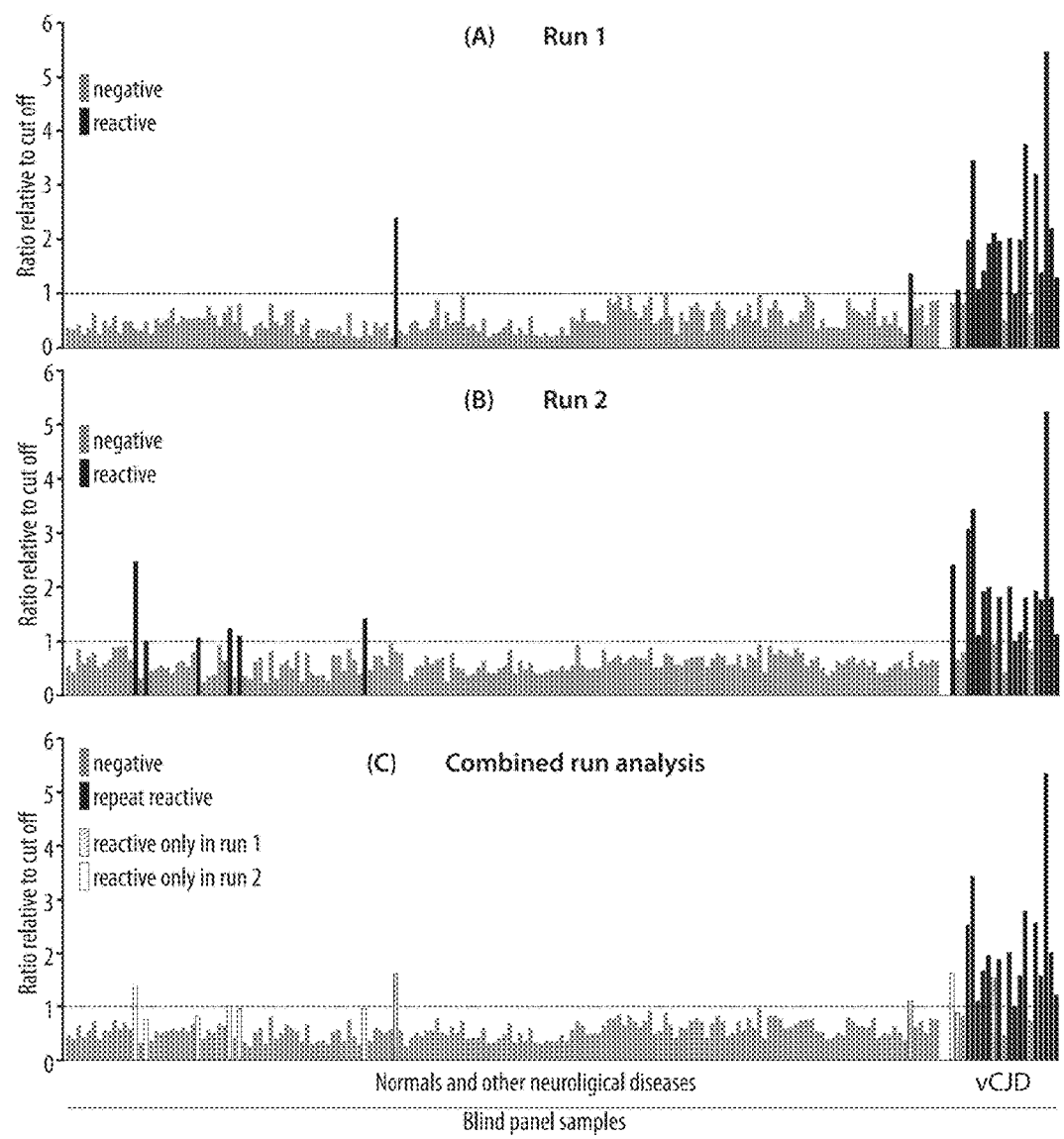
FIG. 3 shows testing a blind panel of 190 samples: A blind panel of 190 blood samples comprising 21 vCJD infected patients, 100 healthy normal controls, and 69 other neurological disease controls were tested in two independent assays. Data are shown as the chemiluminescent signal ratio relative to a cut-off determined from the mean+3xSD of normal controls. Samples shown in grey had a ratio less than 1 and were therefore scored as negative. Panels (A) and (B) represent data from individual assay runs of blind samples. Red bars represent samples with a ratio greater than 1 relative to cut off and scored as reactive. Panel (C) is the combined ratio data of each blind panel sample relative to cut off. Green and blue bars represent samples scored as single reactive in either assay run 1 or assay run 2, respectively. Red bars represent samples scored as repeat reactive in both assays 1 and 2 and were hence scored as positive.

In order to confirm our results and remove any bias from the analysis a panel of 190 samples taken from 21 confirmed vCJD patients (National Prion Clinic), 69 patients with other neurological disease and 100 normal healthy controls (NBS) were blinded by parties independent to the testing and analysis. The samples were tested in batches of 19 samples with internal controls to determine a cut-off threshold for each plate, samples which gave chemiluminescence signals above the cut-off were deemed reactive. To eliminate potential false positive reactions originating not from the sample but from contamination or assay errors each sample was tested twice within independent assay runs (FIG. 3). Only those samples which were repeat reactive in both assays were scored as positive.

From the panel of 190 samples tested a total of 19 and 22 were reactive in assays 1 and 2 respectively (FIG. 3). A subset of 15 of those samples gave signals above the cut-off threshold in both assays and hence were scored positive. Subsequently all 15 positives were decoded as samples obtained from vCJD patients demonstrating an assay sensitivity of 71% (15/21).

Samples from 6 vCJD patients were not identified during testing of the blind panel. Of those samples 3 had been singularly reactive in either assay run 1 or 2 (FIG. 3) potentially indicating a low level of abnormal PrP but not sufficient to be distinguished from controls by the application of a threshold. The 3 remaining samples were scored as negative in both of the test runs and were indistinguishable from normal controls.

None of the normal controls or other neurological disease controls were scored as positive suggesting a high level of specificity. Superficially this could be considered as 100% as none of the controls were scored positive. However, it is important to consider the probability of a negative sample reacting in duplicate assays purely by chance and independent of abnormal PrP content. This rate is provided by the frequency of single reactive samples in each independent assay run and provides a realistic estimation of specificity of 99.97% ($[2/190]_{Assay\ 1} \times [6/190]_{Assay\ 2}$).

Example 4

Direct Detection of Infectivity on Surfaces—Heat Treatment Temperature Determination 1) Prepare stock solution of 100 mg/ml of new batch of steel powder (AISI 304). Wash approximately 3 g in 30 ml 2% triton-x-100 (sigma)/sterile ddH2O in a falcon tube for 2 hours at room temperature. Remove liquid and wash powder 5×10 mins in 30 ml sterile ddH2O on rocking platform. Wash steel in 30 ml 70% ethanol and incubate for 10 mins on rocking platform, then wash again in 3×30 ml sterile ddH2O.
2) Remove small aliquots of 1 ml into eppendorf tubes. Remove all liquid and weigh powder. Resuspend in PBS to give a final concentration of 100 mg/ml powder, aliquot into replica eppendorf tubes giving final mass of steel powder of 23 mg (230 µl of 100 mg/m stock), then remove all liquid.
3) Prepare buffer for dilution of bloods so that final concentration of buffer will be [100 mM Tris pH8.4+ 2% BSA+2% CHAPS+1×complete inhibitors+40 units benzonase (grade II)]
4) Prepare bloods in the above buffer at required dilution so that final volume of blood buffer mix is 800 µl.
5) Add 800 µl of each sample to steel powder aliquots.
6) Incubate steel powder with bloods for at 18° C. o/n at 650 rpm on a thermomixer.
7) Capture steel powder samples with magnetic block and remove supernatant.
8) Wash steel powder samples 2×1 ml PBS/0.05% tween capturing each time on magnetic block. Vortex samples in wash buffer and spin briefly. Wash a further 3×1 ml PBS/0.05% tween capturing each time on magnetic block. Spin samples briefly and remove all liquid.
9) Heat treat all samples of steel powder at 4° C., 20° C., 60° C., 70° C., 80° C., 90° C., 100° C., 110° C. or 120° C. for 5 minutes on a heat block.
10) Allow samples to cool for 3 minutes.
11) Incubate steel powder samples with 50 µl of determined ICSM antibody prepared in PBS/1% tween at 1 µg/ml; for 1 hour at 37° C. and 750 rpm on a thermomixer.
12) Wash steel powder samples 1×1 ml PBS/0.05% tween capturing each time on magnetic block. Add 1 ml PBS/0.05% tween then vortex samples in wash buffer and spin briefly. Remove buffer and wash a further 1×1 ml PBS/0.05% tween capturing each time on magnetic block.
13) Spin briefly and remove all liquid.
14) Incubate steel powder samples with 50 µl of Neutravidin-HRP (Pierce) prepared in PBS/1% tween at 1:100,000 for 45 minutes at 37° C. and 750 rpm on a thermomixer.
15) Prepare a serial dilution series of secondary antibody (1:100,000, 1:1 million and 1:10 million).
16) Wash steel powder samples 1×1 ml PBS/0.05% tween capturing each time on magnetic block. Add 1 ml PBS/0.05% tween then vortex samples in wash buffer and spin briefly. Remove buffer and wash a further 1×1 ml PBS/0.05% tween capturing each time on magnetic block.
17) Mix equal volumes of Supersignal ELISA femto chemiluminescent substrate (Thermo Scientific)
18) Add 60 µl of chemiluminescent substrate to steel powder aliquots, mix thoroughly by pipetting and aliquot into 3×20 µl in 3 replica wells of black ELISA plates (Greiner).
19) To 2 replica wells add 20 µl of each dilution of the secondary antibody dilution series.
20) Add a further 80 µl per well of Supersignal ELISA femto chemiluminescent substrate. Place plate into Tecan M1000 plate reader immediately. Shake for 60 seconds on plate reader tehn read plate on luminescence, attenuation automatic settings.

Example 5

Direct Detection of Infectivity on Surfaces—Dilution Determination

1) Prepare stock solution of 100 mg/ml of new batch of steel powder (AISI 304). Wash approximately 3 g in 30 ml 2% triton-x-100 (sigma)/sterile ddH2O in a falcon tube for 2 hours at room temperature. Remove liquid and wash powder 5×10 mins in 30 ml sterile ddH2O on rocking platform. Wash steel in 30 ml 70% ethanol and incubate for 10 mins on rocking platform, then wash again in 3×30 ml sterile ddH$_2$O.
2) Remove small aliquots of 1 ml into eppendorf tubes. Remove all liquid and weigh powder. Resuspend in PBS to give a final concentration of 100 mg/ml powder, aliquot into replica eppendorf tubes giving final mass of steel powder of 23 mg (230 µl of 100 mg/ml stock), then remove all liquid.
3) Prepare buffer for dilution of bloods as follows so that final concentration of buffer will be [100 mM Tris pH8.4+2% BSA+2% CHAPS+1×complete inhibitors+ 40 units benzonase (grade II)]:
(a) Prepare 100 ml of [200 mM Tris pH8.4+4% BSA+4% CHAPS+4 complete inhibitor tablets+160 units benzonase]
(b) Prepare 50 ml of [110 mM Tris pH8.4+2.2% BSA+ 2.2% CHAPS+complete inhibitors+44units benzonase] by taking 27.5 ml of your 200 mM Tris buffer prepared in (a) and adding 22.5 ml water
(c) Prepare 50 ml of [101 mM Tris pH8.4+2.04% BSA+ 2.04% CHAPS+complete inhibitors+40 units benzonase] by taking 25.3 ml of your 200 mM Tris buffer prepared in (a) and adding 24.7 ml water.
4) Prepare bloods as follows:
(i) Add 400 µl of blood to 400 µl of 200 mM Tris containing buffer (a) this is 1:1 blood buffer mix
(ii) Add 80 µl of blood to 720 µl of 110 mM Tris containing buffer (b) this is 1:10 blood buffer mix
(iii) Add 80 of blood to 792 µl of 101 mM Tris containing buffer (c) this is 1:100 blood buffer mix
5) Add 800 µl of each sample to steel powder aliquots.
6) Incubate steel powder with bloods for at 18° C. o/n at 650 rpm on a thermomixer.
7) Capture steel powder samples with magnetic block and remove supernatant.
8) Wash steel powder samples 2×1 ml PBS/0.05% tween capturing each time on magnetic block. Vortex samples in wash buffer and spin briefly. Wash a further 3×1 ml PBS/0.05% tween capturing each time on magnetic block. Spin samples briefly and remove all liquid.
9) Heat treat all samples of steel powder at determined temperature for 5 minutes on a heat block.
10) Allow samples to cool for 3 minutes.
11) Incubate steel powder samples with 500 of determined ICSM antibody prepared in PBS/1% tween at 1 µg/ml; for 1 hour at 37° C. and 750 rpm on a thermomixer.
12) Wash steel powder samples 1×1 ml PBS/0.05% tween capturing each time on magnetic block. Add 1 ml PBS/0.05% tween then vortex samples in wash buffer and spin briefly. Remove buffer and wash a further 1×1 ml PBS/0.05% tween capturing each time on magnetic block.
13) Spin briefly and remove all liquid.
14) Incubate steel powder samples with 50 µl of Neutravidin-HRP (Pierce) prepared in PBS/1% tween at 1:100,000 for 45 minutes at 37° C. and 750 rpm on a thermomixer.
15) Prepare a serial dilution series of secondary antibody (1:100,000, 1:1 million and 1:10 million).
16) Wash steel powder samples 1×1 ml PBS/0.05% tween capturing each time on magnetic block. Add 1 ml PBS/0.05% tween then vortex samples in wash buffer and spin briefly. Remove buffer and wash a further 1×1 ml PBS/0.05% tween capturing each time on magnetic block.
17) Mix equal volumes of Supersignal ELISA femto chemiluminescent substrate (Thermo Scientific)
18) Add 60 µl of chemiluminescent substrate to steel powder aliquots, mix thoroughly by pipetting and aliquot into 3×20 µl in 3 replica wells of black ELISA plates (Greiner).
19) To 2 replica wells add 20 µl of each dilution of the secondary antibody dilution series.
20) Add a further 80 µl per well of Supersignal ELISA femto chemiluminescent substrate. Place plate into Tecan M1000 plate reader immediately. Shake for 60 seconds on plate reader tehn read plate on luminescence, attenuation automatic settings.

Example 6

Direct Detection of Infectivity on Surfaces—Antibody Determination

1) Prepare stock solution of 100 mg/ml of new batch of steel powder (AISI 304). Wash approximately 3 g in 30 ml 2% triton-x-100 (sigma)/sterile ddH$_2$O in a falcon tube for 2 hours at room temperature. Remove liquid and wash powder 5×10 mins in 30 ml sterile ddH$_2$O on rocking platform. Wash steel in 30 ml 70% ethanol and incubate for 10 mins on rocking platform, then wash again in 3×30 ml sterile ddH$_2$O.
2) Remove small aliquots of 1 ml into eppendorf tubes. Remove all liquid and weigh powder. Resuspend in PBS to give a final concentration of 100 mg/ml powder, aliquot into replica eppendorf tubes giving final mass of steel powder of 23 mg (230 µl of 100 mg/ml stock), then remove all liquid.
3) Prepare 50 ml buffer for dilution of bloods as follows so that final concentration of buffer will be [100 mM Tris pH8.4+2% BSA+2% CHAPS+1×complete inhibitors+40 units benzonase (grade II)]:
4) Add 800 µl of each sample to steel powder aliquots.
5) Incubate steel powder with bloods for at 18° C. o/n at 650 rpm on a thermomixer.
6) Capture steel powder samples with magnetic block and remove supernatant.
7) Wash steel powder samples 2×1 ml PBS/0.05% tween capturing each time on magnetic block. Vortex samples in wash buffer and spin briefly. Wash a further 3×1 ml PBS/0.05% tween capturing each time on magnetic block. Spin samples briefly and remove all liquid.
8) Heat treat all samples of steel powder at determined temperature for 5 minutes on a heat block.
9) Allow samples to cool for 3 minutes.
10) Incubate steel powder samples with 50 µl of either ICSM10B, ICSM18B, ICSM33B or ICSM35B antibody prepared in PBS/1% tween at 1 µg/ml; for 1 hour at 37° C. and 750 rpm on a thermomixer.
11) Wash steel powder samples 1×1 ml PBS/0.05% tween capturing each time on magnetic block. Add 1 ml PBS/0.05% tween then vortex samples in wash buffer and spin briefly. Remove buffer and wash a further 1×1 ml PBS/0.05% tween capturing each time on magnetic block.
12) Spin briefly and remove all liquid.
13) Incubate steel powder samples with 50 µl of Neutravidin-HRP (Pierce) prepared in PBS/1% tween at 1:100,000 for 45 minutes at 37° C. and 750 rpm on a thermomixer.
14) Prepare a serial dilution series of secondary antibody (1:100,000, 1:1 million and 1:10 million).
15) Wash steel powder samples 1×1 ml PBS/0.05% tween capturing each time on magnetic block. Add 1 ml PBS/0.05% tween then vortex samples in wash buffer and spin briefly. Remove buffer and wash a further 1×1 ml PBS/0.05% tween capturing each time on magnetic block.
16) Mix equal volumes of Supersignal ELISA femto chemiluminescent substrate (Thermo Scientific)
17) Add 60 µl of chemiluminescent substrate to steel powder aliquots, mix thoroughly by pipetting and aliquot into 3×20 µl in 3 replica wells of black ELISA plates (Greiner).
18) To 2 replica wells add 20 µl of each dilution of the secondary antibody dilution series.
19) Add a further 80 µl per well of Supersignal ELISA femto chemiluminescent substrate. Place plate into Tecan M1000 plate reader immediately. Shake for 60 seconds on plate reader tehn read plate on luminescence, attenuation automatic settings.

Example 7

Direct Detection of Infectivity on Surfaces—General Protocol

1) Prepare stock solution of 100 mg/ml of new batch of steel powder (AISI 304). Wash approximately 3 g in 30 ml 2% triton-x-100 (sigma)/sterile ddH2O in a falcon tube for 2 hours at room temperature. Remove liquid and wash powder 5×10 mins in 30 ml sterile ddH2O on rocking platform. Wash steel in 30 ml 70% ethanol and incubate for 10 mins on rocking platform, then wash again in 3×30 ml sterile ddH2O.
2) Remove small aliquots of 1 ml into eppendorf tubes. Remove all liquid and weigh powder. Resuspend in PBS to give a final concentration of 100 mg/ml powder, aliquot into replica eppendorf tubes giving final mass of steel powder of 23 mg (230 µl of 100 mg/ml stock), then remove all liquid.
3) Prepare buffer for dilution of bloods so that final concentration of buffer will be [100 mM Tris pH8.4+2% BSA+2% CHAPS+1×complete inhibitors+40 units benzonase (grade II)]
4) Prepare bloods (blood samples) in the above buffer at required dilution so that final volume of sample (blood buffer mix) is 8000.
5) Add 800 µl of each sample to steel powder aliquots.
6) Incubate steel powder with each blood sample for at 18° C. o/n at 650 rpm on a thermomixer.
7) Capture steel powder samples with magnetic block and remove supernatant.
8) Wash steel powder samples 2×1 ml PBS/0.05% tween capturing each time on magnetic block. Vortex samples in wash buffer and spin briefly. Wash a further 3×1 ml PBS/0.05% tween capturing each time on magnetic block. Spin samples briefly and remove all liquid.
9) Heat treat all samples of steel powder at appropriate temperature (see tables above or as determined in example 1) for 5 minutes on a heat block.

10) Allow samples to cool for 3 minutes.
11) Incubate steel powder samples with 50 µl of detection reagent such as primary antibody capable of binding abnormal PrP (e.g. with an appropriate ICSM antibody) prepared in PBS/1% tween at 1 µg/ml; for 1 hour at 37° C. and 750 rpm on a thermomixer.
12) Wash steel powder samples 1×1 ml PBS/0.05% tween capturing each time on magnetic block. Add 1 ml PBS/0.05% tween then vortex samples in wash buffer and spin briefly. Remove buffer and wash a further 1×1 ml PBS/0.05% tween capturing each time on magnetic block.
13) Spin briefly and remove all liquid.
14) Incubate steel powder samples with 50 µl of Neutravidin-HRP (Pierce) prepared in PBS/1% tween at 1:100,000 for 45 minutes at 37° C. and 750 rpm on a thermomixer.
15) Prepare a serial dilution series of secondary detection reagent such as secondary antibody (1:100,000, 1:1 million and 1:10 million).
16) Wash steel powder samples 1×1 ml PBS/0.05% tween capturing each time on magnetic block. Add 1 ml PBS/0.05% tween then vortex samples in wash buffer and spin briefly. Remove buffer and wash a further 1×1 ml PBS/0.05% tween capturing each time on magnetic block.
17) Mix equal volumes of Supersignal ELISA femto chemiluminescent substrate (Thermo Scientific)
18) Add 60 µl of chemiluminescent substrate to steel powder aliquots, mix thoroughly by pipetting and aliquot into 3×20 µl in 3 replica wells of black ELISA plates (Greiner).
19) To 2 replica wells add 20 µl of each dilution of the secondary antibody dilution series.
20) Add a further 80 µl per well of Supersignal ELISA femto chemiluminescent substrate. Place plate into Tecan M1000 plate reader immediately. Shake for 60 seconds on plate reader then read plate on luminescence, attenuation automatic settings.

Discussion of Examples 1 to 7

Our research efforts have focused upon sensitive methods for the detection of vCJD infection in whole blood as this is not only a sample easily obtained for clinical purposes but also the target for protecting the donated blood supply. Through the use of matrix capture and optimised immuno-detection of captured material we have been able to achieve detection of vCJD brain homogenate diluted $10^{10}$-fold in exogenous spiking experiments (FIG. 1). This is approximately 100,000 fold more sensitive than tonsil biopsy and high sensitivity western blotting (21) currently in use at the National Prion Clinic. It is also 10,000 fold beyond the most sensitive immunoassays for vCJD of unknown specificity (31) and more sensitive than conventional rodent bio-assays that typically do not report dilutions of prion-infected brain tissue greater than $10^8$-fold (39). Whilst this may at first appear contradictory rodent bioassays report infectious titre and do not detect PrP molecules directly. The number of PrP monomers that constitute a prion or infectious unit is not fully defined and indeed is likely to be heterogeneous (40). However, it is clear a single infectious unit contains many PrP monomers as an aggregate all of which are potentially available to our assay allowing sensitivity beyond that previously achievable.

As an orphan disease, blood samples from patients with vCJD are scarce and it is impossible to validate assay results with the high numbers of samples typically used in such circumstances. However, we have applied our assay to all the samples available to us, totalling 21, of which 15 were positively identified in our blinded panel, yielding a sensitivity of 71%. Whilst this represents a very significant step forward in prion diagnostics it must be interpreted within the context of associated specificity. Indeed for consideration as a screening assay of blood and tissue donations specificity must exceed a minimum of 99.9% to avoid large numbers of false positive tests resulting in serious ramifications for the individual donors and the related health care agencies.

Our panel contained 100 normal blood samples from the NBS in addition to 69 neurological disease controls. We included samples obtained from patients with Alzheimer's Disease as it has been suggested that abnormal PrP deposition may accompany Aβ accumulation in these diseases (41). Other disorders that may form part of the differential diagnosis for prion disease were also included in the panel. Encouragingly, none of the neurological disease controls provided any reactions in either of the two independent assay runs, single reactive samples being either vCJD or normal controls. Although no false positive results were recorded by our assay criteria a predictive specificity for large scale screening of controls would be approximately 99.97% based on single reactive sample frequencies observed. This level of specificity would be acceptable in clinical use. This could usefully be confirmed with large (1000+) numbers of negative controls.

The blood samples obtained from vCJD patients have to date been taken following the onset of symptoms as at present it is not possible to identify individuals who are definitely infected with vCJD but are currently asymptomatic. There remains therefore the question of when during the pre-clinical silent stage of disease blood is rendered infectious or differentiable from normal controls. The availability of a blood based assay for determining prion disease infection could make it possible to identify preclinical patients infected with vCJD and provide the samples necessary for further assay validation. However, this would be further confounded by our lack of knowledge regarding what a positive assay result would mean in such circumstances and whether a positive assay result would always result in an individual progressing to a clinical onset.

The invention thus represents a major advance in the ability to detect prion infection and provides an assay forming part of a viable clinical blood test.

Example 8

Direct Detection of Infectivity on Surfaces—Detailed Protocol

Note: this protocol is sometimes referred to as the DDA protocol.

1) Prepare stock solution of 100 mg/ml of new batch of steel powder (AISI 304:45 um particles, Goodfellow Product Code: 028-638-41). Wash approximately 3 g in 30 ml 2% v/v Triton X-100 (Sigma Code: T8787) in HPLC Grade ddH$_2$O (VWR Code: 83645.320) in a falcon tube for 2 hours at 30° C. Remove liquid and wash powder 5×10 mins in 30 ml HPLC Grade ddH$_2$O (VWR Code: 83645.320) on rocking platform. Wash steel in 30 ml 70% v/v HPLC grade Ethanol (Fisher Code: E/0665DF/17)/HPLC Grade ddH$_2$O (VWR Code: 83645.320) and incubate for 1 hour on rocking platform, then wash again in 3×30 ml HPLC Grade ddH$_2$O (VWR Code: 83645.320) for 10 mins each.

2) Remove small aliquots of 1 ml into eppendorf tubes. Remove all liquid and weigh powder. Resuspend in PBS (Dulbecco's without Calcium and without Magnesium, GIBCO Code: 14190185 or 14190169) to give a final concentration of 100 mg/ml powder, aliquot into replica eppendorf tubes giving final mass of steel powder of 23 mg (230 μl of 100 mg/ml stock), then remove all liquid. NB—DO NOT ALLOW TO COMPLETELY DRY.
3) Prepare buffer for dilution of bloods as so that final concentration of buffer will be [100 mM Tris pH8.4+ 2% BSA+2% CHAPS+1×complete inhibitors+40 units Benzonase]. Dilutions will vary according to species and strain. Refer to Table A for exemplary conditions.

| i) | Tris | Sigma Code: T1503 |
| --- | --- | --- |
| ii) | BSA | Sigma Code: A7030 |
| iii) | CHAPS | Sigma Code: C3023 |
| iv) | Complete Inhibitors | Roche Code: 1169799801 |
| v) | Benzonase | Merk Code: 70664-250KUN |

4) Add 800 μl of each sample to steel powder aliquots.
5) Incubate steel powder with bloods for at 18° C. O/N at 650 rpm on a Thermomixer.
6) Capture steel powder samples with magnetic block and remove supernatant.
7) Wash steel powder samples 2×1 ml PBS (BDH 10×Stock Box)/0.05% v/v Tween-20 (Sigma Code: P7949) capturing each time on magnetic block. Vortex samples in wash buffer and spin briefly. Wash a further 3×1 ml PBS (BDH 10×Stock Box)/0.05% v/v Tween-20 (Sigma Code: P7949) capturing each time on magnetic block. Spin samples briefly and remove all liquid. NB—DO NOT ALLOW TO COMPLETELY DRY.
8) Heat shock all samples of steel powder at determined temperature for 5 minutes on a heat block. Temperature will vary according to species and strain. Refer to Table A for exemplary conditions.
9) Allow samples to cool for 5 minutes.
10) Incubate steel powder samples with 50 μl of appropriate ICSM antibody prepared in PBS (Dulbecco's without Calcium and without Magnesium, GIBCO Code: 14190185 or 14190169)/1% v/v Tween-20 (Sigma Code: P7949); for 1 hour at 37° C. and 750 rpm on a Thermomixer. Concentration will typically be in the 600 ng/ml to 1 ug/ml range. This will need to determined for each batch of antibody by titration. ICSM antibody will vary according to species and strain. Refer to Table A for exemplary conditions.
11) Wash steel powder samples 1×1 ml PBS (BDH 10×Stock Box)/0.05% v/v Tween-20 (Sigma Code: P7949) capturing each time on magnetic block. Add 1 ml PBS (BDH 10×Stock Box)/0.05% v/v Tween-20 (Sigma Code: P7949) then vortex samples in wash buffer and spin briefly. Remove buffer and wash a further 1×1 ml PBS (BDH 10×Stock Box)/0.05% v/v Tween-20 (Sigma Code: P7949) capturing each time on magnetic block.
12) Spin briefly and remove all liquid.
13) Incubate steel powder samples with 50 μl of Neutravidin-HRP (Pierce Code: PN31030) prepared in PBS (Dulbecco's without Calcium and without Magnesium, GIBCO Code: 14190185 or 14190169))/1% v/v Tween-20 (Sigma Code: P7949) at 1:100,000 dilution for 45 minutes at 37° C. and 750 rpm on a Thermomixer. NB—Antibody is typically used at 1:100,000 fold dilution but this will need to be determined by titration for each new batch,
14) Prepare a serial dilution series of secondary antibody (1:100,000, 1:1 million and 1:10 million).
15) Wash steel powder samples 1×1 ml PBS (BDH 10×Stock Box)/0.05% v/v Tween-20 (Sigma Code: P7949) capturing each time on magnetic block. Add 1 ml PBS (BDH 10×Stock Box)/0.05% v/v Tween-20 (Sigma Code: P7949) then vortex samples in wash buffer and spin briefly. Remove buffer and wash a further 1×1 ml PBS (BDH 10×Stock Box)/0.05% v/v Tween-20 (Sigma Code: P7949) capturing each time on magnetic block.
16) Mix equal volumes of Supersignal ELISA Femto Chemiluminescent Substrate (Pierce Code: PN37074).
17) Add 60 μof Supersignal ELISA Femto Chemiluminescent Substrate (Pierce Code: PN37074) to steel powder aliquots, mix thoroughly by pipetting and aliquot into 3×20 μin 3 replica wells of black ELISA plates (Greiner Code: 655077).
18) To 2 replica wells add 20 μl of each dilution of the secondary antibody dilution series.
19) Add a further 80 μl per well of Supersignal ELISA Femto Chemiluminescent Substrate (Pierce Code: PN37074). Place plate into Tecan M1000 plate reader immediately. Shake for 60 seconds on plate reader then read plate on luminescence, attenuation automatic settings.

TABLE A

Exemplary Conditions

| Species | Dilution | Heat Shock | Antibody |
| --- | --- | --- | --- |
| Mouse (Tg20) | 1:10 | 110 | ICSM10 |
| Mouse (CD1) | 1:10 | 65 | ICSM33 |
| Hamster A | 1:10 | RT | ICSM18 |
| Hamster B | 1:1 | 115 | ICSM18 |
| Sheep | 1:100 | 120 | ICSM33 |
| Human | 1:100 | 110 | ICSM18 |
| Cow | 1:100 | 120 | ICSM18 |

The designations "Hamster A" and "Hamster B" refer to two different preferred embodiments for assaying hamster samples. When the dilution is 1:10, advantageously only a RT heat shock is required; conversely when the dilution is 1:1 then advantageously a 115 Celsius heat shock is used.

TABLE B

Exemplary Reagents

| Description | Quantity | Supplier | Product Code |
| --- | --- | --- | --- |
| Steel Powder AISI 304, 45 um particles | 100 g | Goodfellow | 028-638-41 |
| Bovine Serum Albumin (Fraction V) | 50 g | Sigma | A7030-50g |
| CHAPS | 25 g | Sigma | C3023-25g |
| Benzonase | 1 ml | Merck Chemicals | 70664-250KUN |
| Protease Complete | 20 tablets | Roche Diagnostics | 1169799801 |
| ELISA Femto Chemiluminescence Substrate | 250 ml | Pierce (Fisher) | PN37074 |
| Neutravidin - Conjugated HRP | 500 ul | Pierce (Fisher) | PN31030 |

TABLE B-continued

Exemplary Reagents

| Description | Quantity | Supplier | Product Code |
|---|---|---|---|
| ELISA Plates 96 well Black | 1 case (40) | Greiner Bio-One Ltd | 655077 |
| Plate Sealing film | 1 box (100) | Sigma | Z369695-100EA |
| Triton X100 | 100 ml | Sigma | T8787-100ML |
| Trizma Buffer (Base) | 1 kg | Sigma | T1503-1KG |
| Pure Water (HPLC Grade) | 2.5 l | VWR | 83645.320 |
| Bottled PBS (500 ml) | 10 × 500 ml | GIBCO (Invitrogen) | 14190169 |
| Bottled PBS (100 ml) | 20 × 100 ml | GIBCO (Invitrogen) | 14190185 |
| Ethanol | 2.5 l | Fisher Scientific | E/0665DF/17 |
| Chloros | 5 l | Solmedia | CHL005 |
| 2 ml Screw Cap Eppendorfs | 5000 | Sarstedt Ltd | 72.692 |
| Eppendorf Screw Caps | 1000 | Sarstedt Ltd | 65.716 |
| Pippette Tips (10 ul) | 960 | ANACHEM | RT-10S |
| Pippette Tips (200 ul) | 5 × 1000 | Thistle Scientific | TF-1000-L-R-S-CS |
| Pippette Tips (1000 ml) | 5 × 960 | Thistle Scientific | TF-200-L-R-S-CS |
| Pipette Tips (20 ul) | 5 × 960 | Thistle Scientific | TF-20-L-R-S-CS |
| Nunc Tubes (50 ml) | 450 | Greiner Bio-One Ltd | 210261 |
| Falcom Tubes (15 ml) | 1000 | Greiner Bio-One Ltd | 188271 |
| Tween-20 | 100 ml | Sigma | P7949-100ml |
| ICSM18 Anti-PrP Antibody | 1 mg | D-Gen Ltd | 0130-01810 |

In this example, the invention is demonstrated for sheep.

The standard DDA protocol (e.g. as in Example 8) using biotinylated ICSM33 as a primary antibody, a dilution of blood 1:100 into capture buffer and a heat treatment at 120 C was applied to a range of sheep blood samples taken from 8 known uninfected controls and 8 cases of confirmed scrapie.

All 8 positive samples were distinguishable from negative controls

Data are shown in FIG. 9.

Example 10

The standard DDA protocol (e.g. as in Example 8) using biotinylated ICSM18 as a primary antibody, a dilution of blood 1:100 into capture buffer and a heat treatment at 120 C was applied to a range of cattle blood samples taken from 8 known uninfected controls and 8 cases of confirmed BSE.

All 8 positive samples were distinguishable from negative controls

Data are shown in FIG. 10.

Example 11

In this example, we demonstrate discrimination of vCJD urine from control samples. A standard DDA protocol (e.g. as in Example 8) was carried out using biotinylated ICSM18 as a primary antibody, a dilution of urine 1:1 into capture buffer and a heat treatment at 110 C was applied to a panel of 12 control urine samples and 4 samples collected from vCJD patients. The standard DDA protocol was modified by the use AISI 316 steel in place of the standard AISI 304. AISI 316 gives better results when the sample is urine. A cut-off value was calculated as the mean chemiluminescence signal of the 12 control samples plus 3×standard deviations from the mean.

Three of the four vCJD patient samples were considered positive, i.e. had a ratio of greater than 1.

N.B. Although AISI 304 steel also functions with urine samples, AISI 316 gives superior results.

Figure 11:
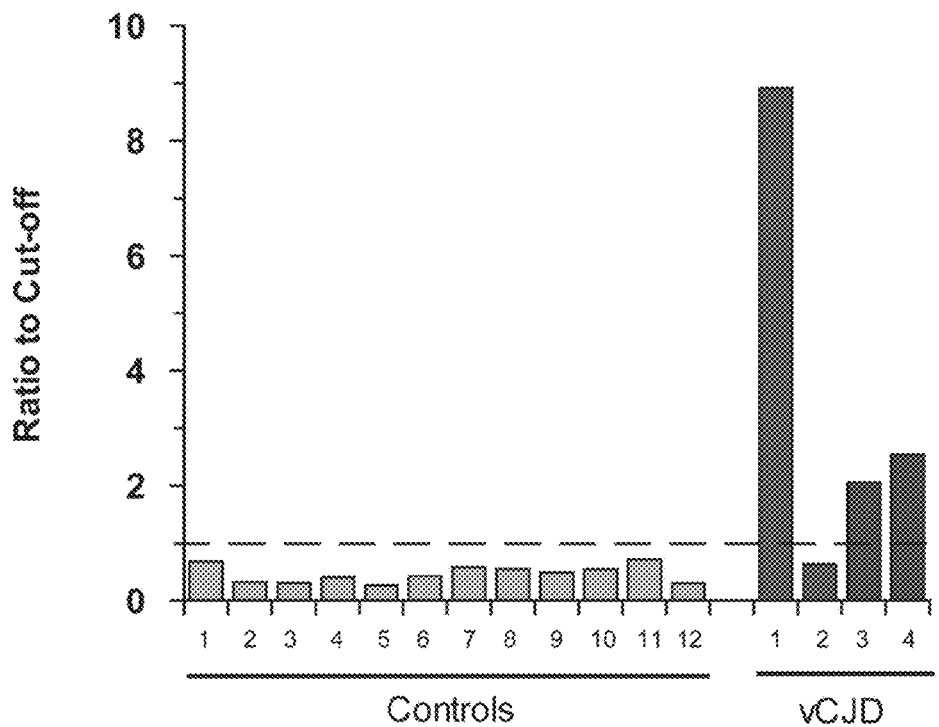
FIG. 11 shows data when urine is the sample.

Data are shown in FIG. 11.

Example 12

In this example, optional DMSO pretreatment is demonstrated.

A potential issue for the methods of the invention is that abnormal PrP is likely to be aggregated into fibrillar structures. A solvent for amyloid is dimethyl sulphoxide (DMSO) and this was investigated as a pre-treatment for samples, in this example blood samples.

8 ul of blood was diluted to 80 ul in 50% v/v DMSO in PBS and incubated at room temperature (21 C) for 4 hours with agitation. The samples were then diluted to final volume of 800 ul in DDA capture buffer containing 15% v/v DMSO. The assay was then performed as described above.

Pre-treatment increases the signal levels obtained from vCJD samples but does not affect control samples, thereby advantageously increasing the levels of differentiation.

Figure 12:
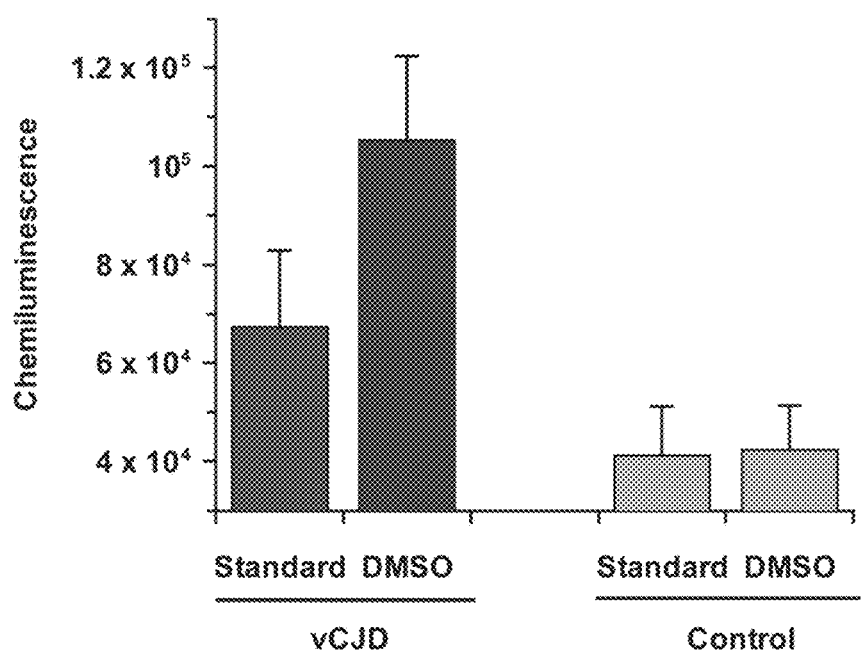
FIG. 12 shows data when optional DMSO pretreatment is applied.

Data are shown in FIG. 12.

Example 13

A typical high throughput and/or automated assay uses a 96-well format. However, such wells are necessarily of a rather small size. This is an advantage for sample processing and space considerations, but the small size restricts the volume available for analysis.

According to the invention, the assay volume can be varied (such as increased) since it is a flexible part of the method. However, it is important to make any volume increases in conjunction with an increased amount of steel particles/powder (i.e. matrix). In other words the ratios of components of the assay are suitably kept within the ranges described above, but by increasing the amount of each of the individual components, a greater volume can be assayed whilst maintaining the ratios of the components within the described ranges.

To demonstrate this, the assay was performed as per the protocol described above (e.g. example 8) with the exception of:

(a) the volume of blood analysed, 8, 12 or 16 ul and hence the blood to capture buffer ratio, ie 1:100, 1:67 and 1:50.

(b) the concentration of steel particles in the capture buffer; 23, 35 or 46 mg/ml.

(c) the chemiluminescence was read in a 24 well plate using 1000 ul of ELISA femto chemiluminescent substrate.

Increasing the volume of blood used in the assay with a fixed steel concentration of 23 mg/ml gives no improvement in signal.

A marginal improvement can be seen with 12 ul of blood and increased steel concentrations.

A significant enhancement is obtained by increasing the input to 16 ul in conjunction with increasing the steel concentration to 46 mg/ml. In this embodiment the input is doubled (8 ul to 16 ul) and the steel is doubled (23 mg to 46 mg) so the proportions remain the same and the capture buffer concentrations remain the same; the net effect is to prepare more of the steel-captured-analyte (the PrP) by use of the larger volumes without altering the core of the method of the invention. Thus the method of the invention can easily be scaled up to larger volumes to suit alternate read-out or assay formats as desired by the skilled worker.

Figures 13, 14:
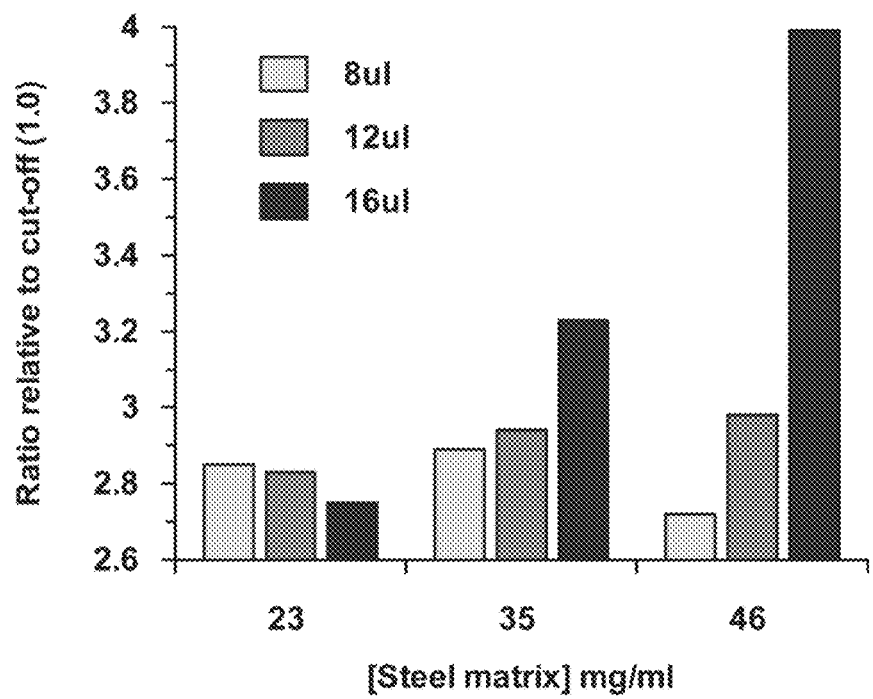
FIG. 13 shows data when different volumes of assay material are prepared.
FIG. 14 shows an exemplary amino acid sequence of human PrP (SEQ ID NO: 7).

Data are shown in FIG. 13.

REFERENCES (1) Prusiner S B. Prions. Proc Natl Acad Sci USA 1998 Nov. 10; 95(23):13363-83.
(2) Collinge J. Prion diseases of humans and animals: their causes and molecular basis. Annu Rev Neurosci 2001; 24:519-50.
(3) Bruce M E, Will R G, Ironside J W, McConnell I, Drummond D, Suttie A et al. Transmissions to mice indicate that 'new variant' CJD is caused by the BSE agent, Nature 1997; 389:498-501.
(4) Hill A F, Desbruslais M, Joiner S, Sidle K C L, Gowland I, Collinge J. The same prion strain causes vCJD and BSE. Nature 1997 Oct. 2; 389:448-50.
(5) World Organisation for Animal Health. Number of cases of bovine spongiform encephalopathy (BSE) reported in the United Kingdom. OiE 2010 Jan. 27; Available from: URL: http://www.oie.int/eng/info/en_esbru.htm
(6) Hilton D A, Ghani A C, Conyers L, Edwards P, McCardle L, Ritchie D et al. Prevalence of lymphoreticular prion protein accumulation in UK tissue samples. J Pathol 2004 July; 203(3):733-9.
(7) Clewley J P, Kelly C M, Andrews N, Vogliqi K, Mallinson G, Kaisar M et al. Prevalence of disease related prion protein in anonymous tonsil specimens in Britain: cross sectional opportunistic survey. BMJ 2009; 338:b1442.
(8) Hill A F, Joiner S, Linehan J, Desbruslais M, Lantos P L, Collinge J. Species barrier independent prion replication in apparently resistant species. Proc Natl Acad Sci USA 2000; 97(18):10248-53.
(9) Race R, Raines A, Raymond G J, Caughey B, Chesebro B. Long-term subclinical carrier state precedes scrapie replication and adaptation in a resistant species: Analogies to bovine spongiform encephalopathy and variant Creutzfeldt-Jakob disease in humans. Journal of Virology 2001 November; 75(21):10106-12.
(10) Frigg R, Klein M A, Hegyi I, Zinkernagel R M, Aguzzi A. Scrapie pathogenesis in subclinically infected B-Cell-deficient mice. Journal of Virology 1999 November; 73(11):9584-8.
(11) Peden A, McCardle L, Head M W, Love S, Ward H J, Cousens S N et al. Variant CJD infection in the spleen of a neurologically asymptomatic UK adult patient with haemophilia. Haemophilia 2010 Jan. 12.
(12) Collinge J, Whitfield J, McKintosh E, Beck J, Mead S, Thomas D J et al. Kuru in the 21st century—an acquired human prion disease with very long incubation periods. Lancet 2006 Jun. 24; 367(9528):2068-74.
(13) Llewelyn C A, Hewitt P E, Knight R S, Amar K, Cousens S, Mackenzie J et al. Possible transmission of variant Creutzfeldt-Jakob disease by blood transfusion. Lancet 2004 Feb. 7; 363(9407):417-21.
(14) Peden A H, Head M W, Ritchie D L, Bell J E, Ironside J W. Preclinical vCJD after blood transfusion in a PRNP codon 129 heterozygous patient. Lancet 2004 Aug. 7; 364(9433):527-9.
(15) Wroe S J, Pal S, Siddique D, Hyare H, Macfarlane R, Joiner S et al. Clinical presentation and pre-mortem diagnosis of variant Creutzfeldt-Jakob disease associated with blood transfusion: a case report. Lancet 2006 Dec. 9; 368(9552):2061-7.
(16) Hewitt P E, Llewelyn C A, Mackenzie J, Will R G. Creutzfeldt-Jakob disease and blood transfusion: results of the UK Transfusion Medicine Epidemiological Review study. Vox Sang 2006 October; 91(3):221-30.
(17) Prusiner S B. Novel proteinaceous infectious particles cause scrapie. Science 1982; 216:136-44.
(18) Soto C. Diagnosing prion diseases: needs, challenges and hopes. Nat Rev Microbial 2004 October; 2(10): 809-19.
(19) Wadsworth J D, Joiner S, Fox K., Linehan J, Desbruslais M, Brandner S et al. Prion infectivity in variant Creutzfeldt-Jakob disease rectum. Gut 2007 January; 56(1):90-4.
(20) Tattum M H, Jones S, Pal S, Collinge J, Jackson G S. Discrimination between prion-infected and normal blood samples by protein misfolding cyclic amplification. Transfusion 2010 Feb. 18; Electronic publication ahead of print.
(21) Wadsworth J D, Joiner S, Hill A F, Campbell T A, Desbruslais M, Luthert P J et al. Tissue distribution of protease resistant prion protein in variant CJD using a highly sensitive immuno-blotting assay. Lancet 2001; 358(9277):171-80.
(22) Brown P, Rohwer R G, Dunstan B C, MacAuley C, Gajdusek D C, Drohan W N. The distribution of infectivity in blood components and plasma derivatives in experimental models of transmissible spongiform encephalopathy. Transfusion 1998 September; 38(9): 810-6.
(23) Brown P, Cervenáková L, McShane L M, Barber P, Rubenstein R, Drohan W N. Further studies of blood infectivity in an experimental model of transmissible spongiform encephalopathy, with an explanation of why blood components do not transmit Creutzfeldt-Jakob disease in humans. Transfusion 1999 November; 39(11-12):1169-78.
(24) Prusiner S B. Prions. Proc Natl Acad Sci USA 1998 Nov. 10; 95(23):13363-83.
(25) Safar J, Wille H, Itri V, Groth D, Serban H, Torchia M et al. Eight prion strains PrP$^{Sc}$ molecules with different conformations. Nat Med 1998; 4(10):1157-65.
(26) Safar J G, Geschwind M D, Deering C, Didorenko S, Sattavat M, Sanchez H et al. Diagnosis of human prion disease. Proc Natl Acad Sci USA 2005 Mar. 1; 102(9): 3501-6.
(27) Nazar K E, Kuhn F, Seward T, Green M, Zwald D, Purro M et al. Immunodetection of disease-associated mutant PrP, which accelerates disease in GSS transgenic mice. EMBO J 2005 Jul. 6; 24(13):2472-80.
(28) Pastrana M A, Sajnani G, Onisko B, Castilla J, Morales R, Soto C et al. Isolation and Characterization of a Proteinase K-Sensitive PrP(Sc) Fraction. Biochemistry 2006 Dec. 26; 45(51):15710-7.
(29) Thackray, A M, Hopkins L, Bujdoso R. Proteinase K-sensitive disease-associated ovine prion protein revealed by conformation-dependent immunoassay. Biochem J 2007 Jan. 10; 401(2):475-83.
(30) Cronier S, Gros N, Tattum M H, Jackson G S, Clarke A R, Collinge J et al. Detection and characterization of proteinase K-sensitive disease-related prion protein with thermolysin. Biochem J 2008 Aug. 6; 416(2):297-305.
(31) Tattum M H, Jones S, Pal S, Khalili-Shirazi A, Collinge J, Jackson G S. A highly sensitive immunoassay for the detection of prion infected material in whole human blood without the use of proteinase K. Transfusion 2010 Jun. 1; (In Press).
(32) Flechsig E, Hegyi I, Enari M, Schwarz P, Collinge J, Weissmann C. Transmission of scrapie by steel-surface-bound prions. Molecular Medicine 2001 October; 7(10):679-84.
(33) Zobeley E, Flechsig E, Cozzio A, Masato E, Weissmann C. Infectivity of scrapie prions bound to a stainless steel surface. Molecular Medicine 1999 Feb. 23; 5:240-3.
(34) Edgeworth J A, Jackson G S, Clarke A R, Weissmann C, Collinge J. Highly sensitive, quantitative cell-based assay for prions adsorbed to solid surfaces. Proc Natl Acad Sci USA 2009 Feb. 9; 106(9):3479-83.
(35) Poser S, Mollenhauer B, Krauss A, Zerr I, Steinhoff B J, Schroeter A et al. How to improve the clinical diagnosis of Creutzfeldt-Jakob disease. Brain 1999 December; 122(12):2345-51.
(36) Hewitt P E, Llewelyn C A, Mackenzie J, Will R G. Three reported cases of variant Creutzfeldt-Jakob disease transmission following transfusion of labile blood components. Vox Sang 2006 November; 91 (4):348.
(37) Gregori L, McCombie N, Palmer D, Birch P, Sowemimo-Coker S O, Giulivi A et al. Effectiveness of leucoreduction for removal of infectivity of transmissible spongiform encephalopathies from blood. Lancet 2004 Aug. 7; 364(9433):529-31.
(38) Gregori L, Gurgel P V, Lathrop J T, Edwardson P, Lambert B C, Carbonell R G et al. Reduction in infectivity of endogenous transmissible spongiform encephalopathies present in blood by adsorption to selective affinity resins. Lancet 2006 Dec. 23; 368 (9554):2226-30.
(39) Prusiner S B, Cochran S P, Groth D F, Downey D E, Bowman K, Martinez H M. Measurement of the scrapie agent using an incubation time interval assay. Ann Neurol 1982; 11:353-38.
(40) Silveira J R, Raymond G J, Hughson A G, Race R E, Sim V L, Hayes S F et al. The most infectious prion protein particles. Nature 2005 Sep. 8; 437(7056):257-61.
(41) Barcikowska B, Kwiecinski H, Liberski P P, Kowalski J, Brown P, Gajdusek D C. Creutzfeldt-Jakob disease with Alzheimer-type Aβ-reactive amyloid plaques. Histopathology 1995; 26:445-50.

All publications mentioned in the above specification are herein incorporated by reference. Various modifications and variations of the described aspects and embodiments of the present invention will be apparent to those skilled in the art without departing from the scope of the present invention. Although the present invention has been described in connection with specific preferred embodiments, it should be understood that the invention as claimed should not be unduly limited to such specific embodiments. Indeed, various modifications of the described modes for carrying out the invention which are apparent to those skilled in the art are intended to be within the scope of the following claims.

The invention claimed is:

1. A method for detection of abnormal prion protein (PrP) in a sample of blood, said method comprising:
   (a) diluting the sample in the range of 1:10 to 1:100, inclusive, with buffer to comprise final concentrations of
      (i) 10 mM to 500 mM buffer agent;
      (ii) 1% to 10% w/v bovine serum albumin; and
      (iii) 1% to 8% w/v 3-[(3-cholamidopropyl)dimethylammonio]-1-propanesulfonate (CHAPS); and
      wherein said buffer does not include chaotropic agents or proteinases;
   (b) adding steel particles and incubating to allow PrP binding;
   (c) washing the steel particles to remove diluted sample;
   (d) heating the steel particles to 110°C. for 5 minutes; and
   (e) detecting abnormal PrP captured on the steel particles using antibody or a fragment thereof capable of binding said abnormal PrP;
   wherein said method is practiced without use of chaotropic agents or proteinases.

2. The method according to claim 1 wherein step (a) comprises diluting the sample with buffer to comprise final concentrations of
   (i) 50 mM to 200 mM buffer agent;
   (ii) 1% to 4% w/v bovine serum albumin; and
   (iii) 2% to 4% w/v CHAPS.

3. The method according to claim 1 wherein step (a) comprises diluting the sample with buffer to comprise final concentrations of
   (i) 100 mM buffer agent;
   (ii) 2% w/v bovine serum albumin; and
   (iii) 2% w/v CHAPS.

4. The method according to claim 1, wherein the blood is from a human and the blood sample is diluted with buffer at 1:100.

5. The method according to claim 1, wherein the buffer further comprises protease inhibitors.

6. The method according to claim 1, wherein the antibody of step (e) is selected from the group consisting of ICSM10, ICSM18, ICSM33, and ICSM35.

7. The method according to claim 6, wherein the sample is from a human and the antibody is ICSM18 or a fragment thereof.

8. The method according to claim 1, wherein the steel particles comprise American Iron and Steel Institute (AISI) 304 stainless steel.

9. The method according to claim 1, wherein the buffer agent is tris(hydroxymethyl)aminomethane (Tris).

10. The method according to claim 1, wherein the buffer is pH 8.4.

* * * * *